(12) United States Patent
Hamdouchi et al.

(10) Patent No.: US 9,809,592 B2
(45) Date of Patent: Nov. 7, 2017

(54) ISOPROPYL TRIAZOLO PYRIDINE COMPOUNDS

(71) Applicant: Eli Lilly and Company, Indianapolis, IN (US)

(72) Inventors: Chafiq Hamdouchi, Carmel, IN (US); Pranab Maiti, West Bengal (IN); Anne Reifel Miller, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/106,953

(22) PCT Filed: Jan. 6, 2015

(86) PCT No.: PCT/US2015/010277
§ 371 (c)(1),
(2) Date: Jun. 21, 2016

(87) PCT Pub. No.: WO2015/105779
PCT Pub. Date: Jul. 16, 2015

(65) Prior Publication Data
US 2016/0333005 A1    Nov. 17, 2016

Related U.S. Application Data

(60) Provisional application No. 61/925,797, filed on Jan. 10, 2014.

(51) Int. Cl.
*A61K 31/437* (2006.01)
*C07D 471/04* (2006.01)

(52) U.S. Cl.
CPC ................... *C07D 471/04* (2013.01)

(58) Field of Classification Search
CPC ..................... A61K 31/437; C07D 471/04
USPC .......................................... 514/303; 546/119
See application file for complete search history.

(56) References Cited

FOREIGN PATENT DOCUMENTS

| EP | 1559422 | 3/2005 |
|---|---|---|
| WO | 2004/041266 | 5/2004 |
| WO | 2005/086661 | 9/2005 |
| WO | 2009/153496 | 12/2009 |
| WO | 2011/161030 | 12/2011 |
| WO | 2013/119040 | 8/2013 |
| WO | 2015/088868 | 6/2015 |
| WO | 2015/105786 | 7/2015 |

*Primary Examiner* — Brenda Coleman
(74) *Attorney, Agent, or Firm* — MaCharri Vorndran-Jones

(57) ABSTRACT

The present invention provides a compound of the Formula (I) below: Wherein $R^1$ is selected from the group consisting of H, $CH_3$, CN, $CH_2CN$, $C(CH_3)_2CN$, and F; $R^2$ is selected from the group consisting of H, $O(C_1$-$C_3$alkyl)$R^5$, $CH_2CN$, and CN; $R^3$ is selected from the group consisting of H, $OCH_3$, CN, $C(CH_3)_2CN$, and $CH_2CN$; $R^4$ is selected from the group consisting of H and $CH_3$; $R^5$ is selected from the group consisting of H, CN, $C(CH_3)_2CN$, $OCH_3$, $S(O)_2CH_3$, and $C(CH_3)_2OH$; provided that at least one selected from the group consisting of R1, R2, R3 and R4 is H; or a pharmaceutically acceptable salt thereof, methods of treating diabetes using the compound and a process for preparing the compound.

(I)

17 Claims, No Drawings

ISOPROPYL TRIAZOLO PYRIDINE COMPOUNDS

This invention relates to triazolo-pyridine compounds or pharmaceutically acceptable salts thereof, and for use of compounds in therapy. Triazolo-pyridine compounds of this invention are activators of GPR-40.

GPR-40, also known as Free Fatty Acid Receptor 1 (FFA1 or FFAR1), is reported as predominately expressed at high levels in rodent pancreatic beta cells, insulinoma cell lines, and human islets. The glucose modulation of insulin secretion is an important feature of activating GPR-40. Compounds that effectuate GPR-40 activation are associated with stimulation of insulin secretion in a patient with type II diabetes (T2D). Compounds that are GPR-40 activators are desired for use in treatment of GPR-40 mediated conditions.

WO2004/041266 discloses GPR-40 receptor function regulators comprising a compound having an aromatic ring and a group capable of releasing a cation.

The present invention provides a compound of the Formula I below:

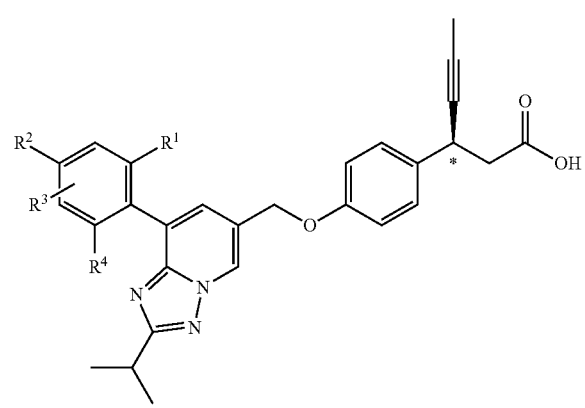

I

Wherein $R^1$ is selected from the group consisting of H, $CH_3$, CN, $CH_2CN$, $C(CH_3)_2CN$, and F;

$R^2$ is selected from the group consisting of H, $O(C_1-C_3 alkyl)R^5$, $CH_2CN$, and CN;

$R^3$ is selected from the group consisting of H, $OCH_3$, CN, $C(CH_3)_2CN$, and $CH_2CN$;

$R^4$ is selected from the group consisting of H and $CH_3$; and $R^5$ is selected from the group consisting of H, CN, $C(CH_3)_2CN$, $OCH_3$, $S(O)_2CH_3$, and $C(CH_3)_2OH$; provided that at least one selected from the group consisting of R1, R2, R3 and R4 is H;

or a pharmaceutically acceptable salt thereof.

The compounds of the present invention have a chiral carbon identified in the structure above with an asterisk (*). Preferred compounds have the configuration shown above, which by convention is known as the S configuration. For avoidance of doubt, the present invention embraces all chiral carbon configurations, as illustrated by Formula Ia:

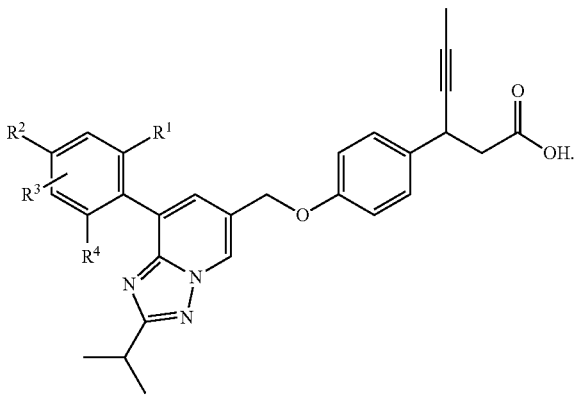

Ia

In an embodiment $R^1$ is selected from the group consisting of H, $CH_3$ and F. In an embodiment $R^1$ is selected from the group consisting H and $CH_3$.

In another embodiment $R^2$ is selected from the group consisting of H, and $-O(C_1-C_3 alkyl)R^5$. In an embodiment $R^2$ is selected from the group consisting of H and $OCH_3$. In an embodiment $R^5$ is selected from the group consisting of H, $-S(O)_2CH_3$, and $-C(CH_3)_2OH$.

Another embodiment is a compound wherein $R^3$ is H, $R^1$ is $CH_3$ and $R^4$ is $CH_3$. In another embodiment $R^3$ is H, $R^1$ is $CH_3$, $R^4$ is $CH_3$, and $R^2$ is $-OCH_3$.

In an embodiment $R^3$ is selected from the group consisting of H and $OCH_3$. In an embodiment $R^3$ is H.

In an embodiment $R^4$ is $CH_3$. A compound wherein $R^1$ is $CH_3$, $R^2$ is H or $-OCH_3$, $R^3$ is H and $R^4$ is $CH_3$ is an embodiment. In an embodiment $R^1$ is $CH_3$ and $R^4$ is $CH_3$.

One preferred compound of the present invention is (S)-3-{4-[2-Isopropyl-8-(4-methoxy-2,6-dimethyl-phenyl)-[1,2,4]triazolo[1,5-a]pyridin-6-ylmethoxy]-phenyl}-hex-4-ynoic acid, or a pharmaceutically acceptable salt thereof. One preferred compound of the present invention is (S)-3-{4-[8-(2,6-Dimethyl-phenyl)-2-isopropy]-[1,2,4]triazolo[1,5-a]pyridin-6-ylmethoxy]-phenyl}-hex-4-ynoic acid, or a pharmaceutically acceptable salt thereof.

The present invention also provides a pharmaceutical composition comprising a compound of Formula I as described above or a pharmaceutically acceptable salt thereof together with one or more pharmaceutically acceptable carriers, diluents or excipients.

The present invention also provides a pharmaceutical composition comprising a compound of Formula I as described above or a pharmaceutically acceptable salt thereof together with one or more pharmaceutically acceptable carriers, diluents or excipients, and optionally one or more therapeutic agents. Additional therapeutic agents include for example, metformin and/or Januvia.

The present invention also provides a method for treating diabetes in a mammal. The method comprises administering to the mammal in need of treatment an effective amount of a compound as described above for Formula I, or a pharmaceutically acceptable salt thereof. More preferably the present invention provides a method of treating type two diabetes in a mammal in need of treatment comprising administering an effective amount of a compound as described above for Formula I or a pharmaceutically acceptable salt thereof.

The present invention provides a compound according to Formula I or a pharmaceutically acceptable salt thereof as described above for use in therapy.

In yet another form, the present invention provides a compound as described above according to Formula I, a pharmaceutically acceptable salt thereof, or pharmaceutical composition for use in the treatment of diabetes in a mammal in need thereof. Preferably the use is for the treatment of type two diabetes and the mammal is a human.

The present invention provides use of a compound according to Formula I, or a pharmaceutically acceptable salt thereof, in the manufacture of a medicament for the treatment of diabetes. Preferably the medicament is for the treatment of type two diabetes.

In yet another form, the present invention provides an intermediate compound of the Formula II

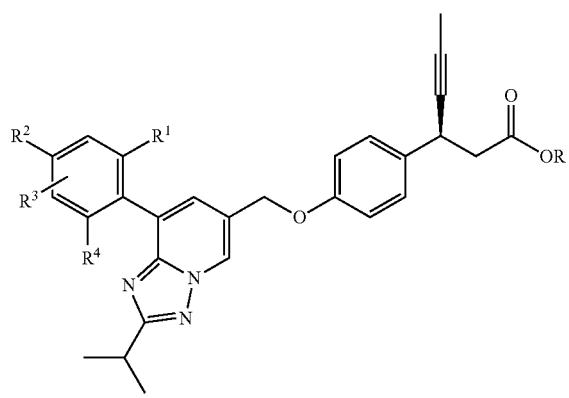

II wherein $R^1$ is selected from the group consisting of H, $CH_3$, CN, $CH_2CN$, $C(CH_3)_2CN$, and F;

$R^2$ is selected from the group consisting of H, $O(C_1-C_3 alkyl)$ $R^5$, $CH_2CN$, and CN;

$R^3$ is selected from the group consisting of H, $OCH_3$, CN, $C(CH_3)_2CN$, and $CH_2CN$;

$R^4$ is selected from the group consisting of H and $CH_3$;

$R^5$ is selected from the group consisting of H, CN, $C(CH_3)_2CN$, $OCH_3$, $S(O)_2CH_3$, and $C(CH_3)_2OH$; provided that at least one selected from the group consisting of R1, R2, R3 and R4 is H; and R is selected from the group consisting of $C_{1-4}$ alkyl, $C_{1-4}$ haloalkyl, $C_{3-6}$ cycloalkyl, $C_1-C_4$ alkyl-$C_{3-6}$ cycloalkyl, phenyl, and $C_{1-5}$ alkylphenyl to provide a compound of Formula I, or a pharmaceutically acceptable salt thereof. Preferred R groups include $C_{1-2}$ alkyl, —$C_{1-2}$ haloalkyl, phenyl, and $C_{1-2}$ alkylphenyl. Particularly preferred R groups include methyl, ethyl, phenyl, and benzyl; or a pharmaceutically acceptable salt thereof.

The present invention also provides a process or method for preparing a compound described above for Formula I. The method comprises de-protecting or de-esterifying the intermediate compound according to Formula II to prepare the compound of Formula 1, or a pharmaceutically acceptable salt thereof.

One skilled in the art would readily understand and be able to implement de-protecting reactions without undue experimentation. It will be recognized by those skilled in the art that in addition to the carboxylic acid and protected carboxylic acid, other functional groups that can be readily converted to a carboxylic acid can be used in place of the carboxylic acid or protected acid. Such functional groups, preparations, and transformations of these groups to carboxylic acids can be found in "Comprehensive Organic Transformations: A Guide to Functional Group Preparations" by Larock. R. C, Wiley VCH, 1999 and in "March's Advanced Organic Chemistry, Reactions, Mechanisms and Structure" Smith, M. B., and March, J., Wiley-Interscience, 6th Ed. 2007.

A compound of the present invention can be provided as a pharmaceutically acceptable salt. "Pharmaceutically acceptable salt" refers to salts of the compound of the invention considered to be acceptable for clinical and/or veterinary use. Pharmaceutically acceptable salts and common methodology for preparing them are well known in the art. See, e.g., P. Stahl, et al., Handbook of Pharmaceutical Salts: Properties, Selection and Use, (VCHA/Wiley-VCH, 2002); S. M. Berge, et al., "Pharmaceutical Salts," *Journal of Pharmaceutical Sciences*, Vol. 66, No. 1, January 1977.

Individual isomers, enantiomers, or diastereomers may be separated at any convenient point in the synthesis of the compound of Formula I by methods such as chiral chromatography. Additionally, the intermediates described in the following Schemes and preparations contain a number of nitrogen, hydroxy, and acid protecting groups such as esters. The variable protecting group may be the same or different in each occurrence depending on the particular reaction conditions and the particular transformations to be performed. The protection and deprotection conditions are well known to the skilled artisan and are described in the literature. See. e.g., Greene and Wuts, *Protective Groups in Organic Synthesis*, (T. Greene and P. Wuts, eds., 2d ed. 1991).

The abbreviations used herein are defined according to *Aldrichimica Acta*, Vol. 17, No. 1, 1984. Other abbreviations are defined as follows: "ADDP" refers to 1-(azodicarbonyl) dipiperidine; "BSA" refers to Bovine Serum Albumin; "n-BuLi" refers to n-butyl lithium; "DIBAL" refers to diisobutylaluminum hydride; "DCM" refers to dichloromethane; "DMEM" refers to Dulbecco's Modified Eagle's Medium; "DMF" refers to dimethylformamide; "DEAD" refers to diethyl azodicarboxylate; "DMF" refers to dimethylformamide; "DMSO" refers to dimethylsulfoxide; "$EC_{50}$" refers to the effective concentration at half the maximal response; "EtOAc" refers to ethyl acetate; "EtOH" refers to ethyl alcohol or ethanol; "F12" refers to Ham's F12 medium; "FA" refers to fatty acid; "FBS" refers to Fetal Bovine Serum; "HEK" refers to human embryonic kidney; "$IC_{50}$" refers to the concentration of an agent that produces 50% of the maximal inhibitory response possible for that agent; "MeOH" refers to methyl alcohol or methanol; "MTBE" refers to methyl t-butyl ether; "NBS" refers to N-bromosuccinimide; "Pd(amphos)$Cl_2$" refers to bis(di-tert-butyl(4-dimethylaminophenyl)phosphine)dichloropalladium (II); "Pd(dppf)$Cl_2$" refers to [1,1'-bis(diphenylphosphino)ferrocene-palladium(II) dichloride; "Pd($PPh_3$)$_2Cl_2$" refers to bis(triphenylphosphine)palladium(II) chloride; "PPAR" refers to peroxisome proliferator-activated receptor; "PPRE" refers to peroxisome proliferator response element; "RFU" refers to relative fluorescence unit; "RPMI" refers to Roswell Park Memorial Institute; "TFA" refers to trifluoroacetic acid; "THF" refers to tetrahydrofuran; "TK" refers to thymidine kinase; and "TAK875" refers to the Takeda compound known as fasiglifam.

The term alkyl as used herein is a straight chain alkyl such as ethyl or n-propyl, or a branched chain alkyl such as isopropyl or tert-butyl. The term $C_{1-4}$ haloalkyl refers to an alkyl group that has 1, 2, 3, or more halo groups attached to the carbons of the alkyl chain. If there are two or more halogens the halogens need not be attached to the same carbon. This term also includes perhalo alkyls where all the hydrogen atoms of the alkyl group are replaced with a halogen.

In the schemes below, all substituents unless otherwise indicated, are as previously defined. The reagents and starting materials are generally readily available to one of ordinary skill in the art. Others may be made by standard techniques of organic and heterocyclic chemistry which are analogous to the syntheses of known structurally-similar compounds and the procedures described in the Preparations and Examples which follow including any novel procedures.

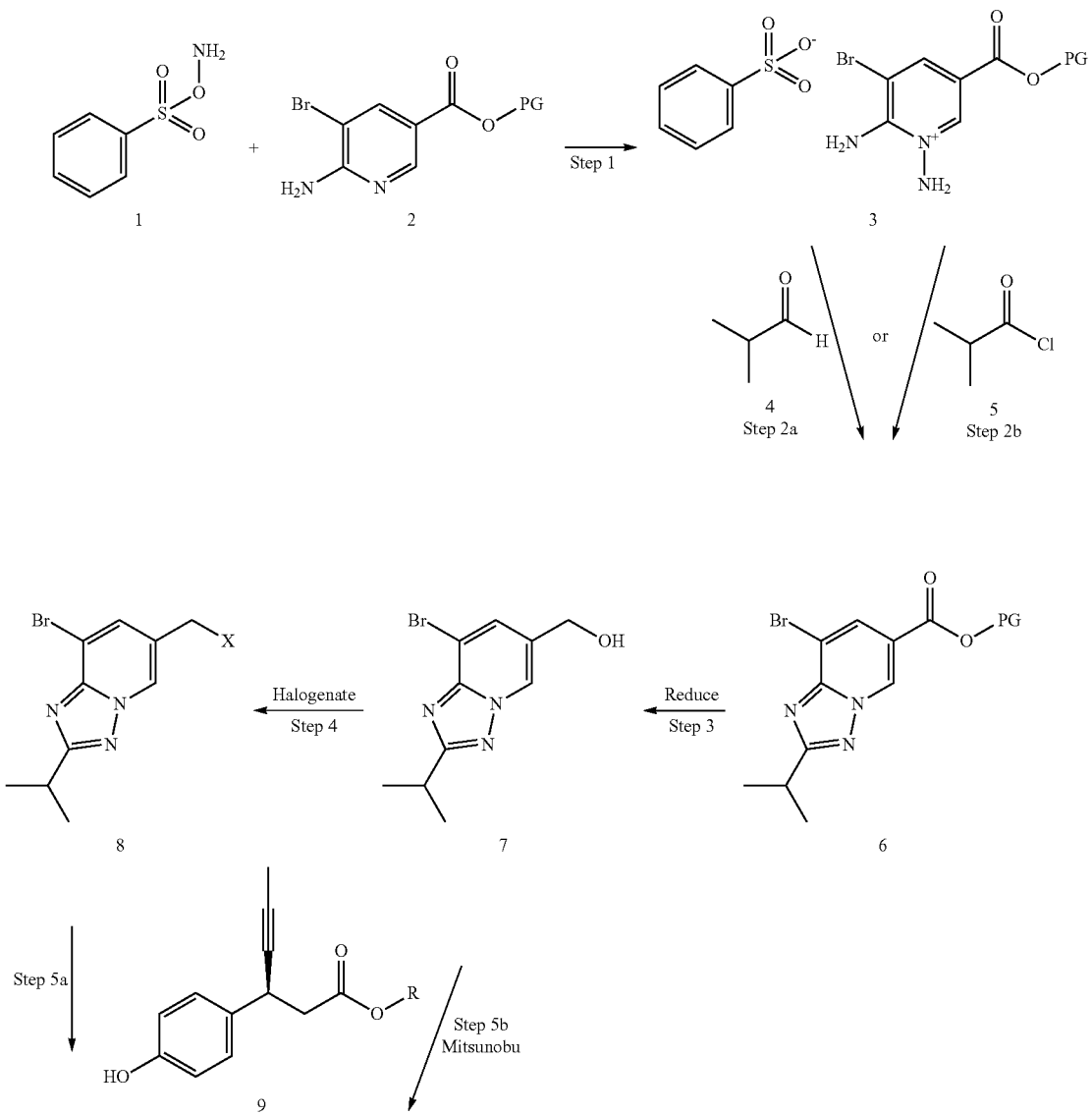

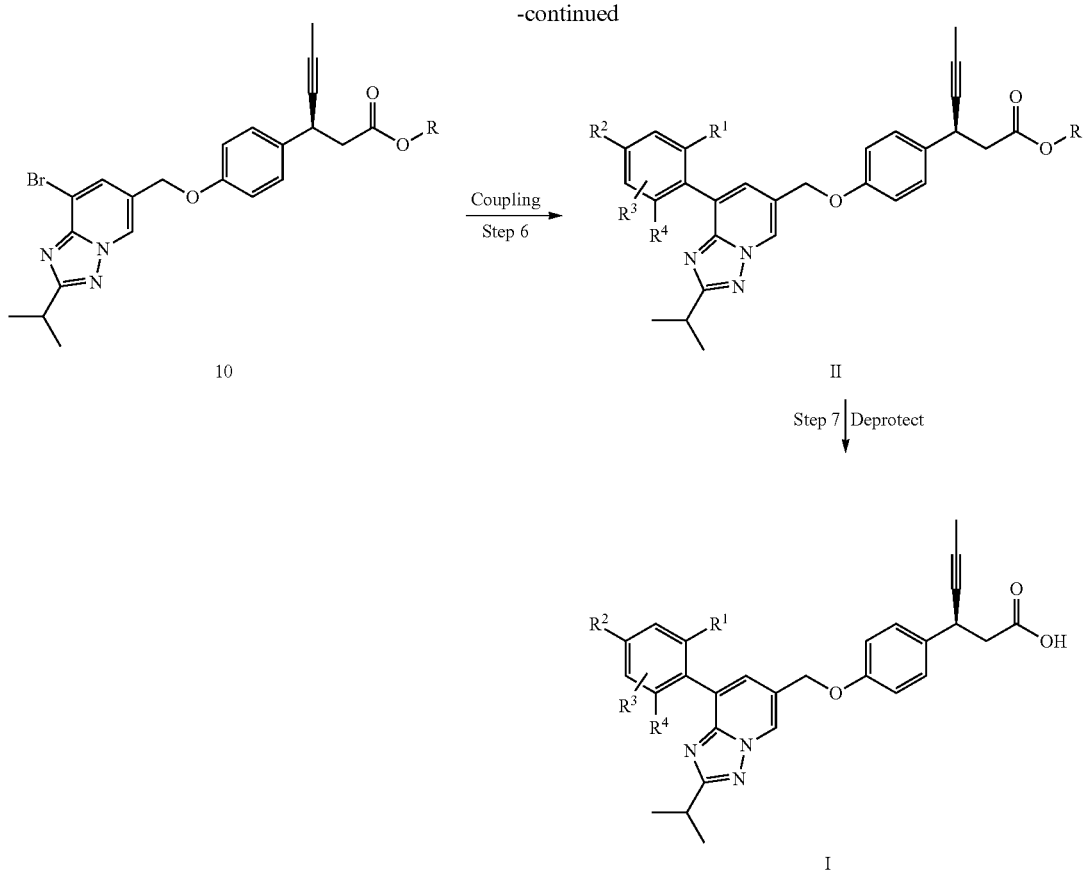

PG = Protecting group
X = Cl, Br

A compound of Formula I can be prepared in accordance with reactions as depicted in Scheme 1. PG is a protecting group developed for an acid such as esters, see above. Scheme 1 (Step 1) depicts the formation of the of the phenyl sulfonic acid substituted diamino pyridine quaternary salt. A mono methyl or trimethyl phenyl aminosulfonate (1) can be reacted with a substituted 2-amino pyridine (2) to provide a diamino pyridine quaternary salt (3). The quaternary salt (3) can then be reacted with 2-methylpropanal (4, Step 2a) in an organic base such as triethylamine using a polar protic solvent such as MeOH to form the substituted [1,2,4]triazolo[1,5-a]pyridine (6). Alternatively 2-methylpropanoyl chloride (5, Step 2b) can be reacted with the quaternary salt (3) in a basic organic solvent such as pyridine to form the substituted [1,2,4]triazolo[1,5-a]pyridine (6). The ester of compound (6) can be reduced to the methyl hydroxy under standard conditions using a reducing agent such as diisobutyl aluminum hydride (DIBAL) at a temperature such as −78° C. in a polar aprotic solvent such as DCM to give the hydroxy compound (7, Step 3). Other reducing reagents well known in the art are lithium aluminum hydride or sodium borohydride. Compound (7) can be alkylated under Mitsunobu conditions to the ether (10, Step 5b). Mitsunobu conditions are well known in the art and involve reacting an alcohol (7) with a nucleophile such as a phenol (9) using a phosphine such as triphenyl phosphine, tributyl phosphine, or triethylphosphine and an azodicarboxylate such as diethyl azodicarboxylate (DEAD) or diisopropyl azodicarboxylate (DIAD) or an azodicarbonyl such as ADDP. Alternatively the alcohol (7) can be converted to a halogen (8, Step 4) such as bromide or chloride using thionyl chloride to form the chloride or phosphorus tribromide in DCM to form the bromide. The halogenated compound (8) can then be alkylated with the phenol (9) under basic conditions using an inorganic base such as cesium carbonate or potassium acetate in a polar aprotic solvent such as acetonitrile to give compound (10, Step 5a). The 8-halogen substituted [1,2,4]triazolo[1,5-a]pyridine (10) can be coupled under Suzuki-Miyaura cross coupling conditions using a boronic acid reagent. The skilled artisan will recognize that there are a variety of conditions useful for facilitating such cross coupling reactions. Accordingly, a suitable palladium reagent includes bis(triphenylphosphine)palladium(II) dichloride, Pd(amphos)Cl$_2$, tris(dibenzylideneacetone)dipalladium (0) with tricyclohexylphosphine, (1,1'-bis(diphenylphosphino)ferrocene)palladium (II) chloride, palladium tetrakistriphenylphosphine, or palladium(II) acetate. A suitable base includes cesium carbonate, sodium carbonate, potassium carbonate, or potassium phosphate tribasic monohydrate in a suitable non-polar solvent such as 1,4-dioxane to give the 8-substituted [1,2,4]triazolo[1,5-a]pyridine (II, Step 6). The protected acid of II can be deprotected under standard basic conditions well known in the art to give compounds of Formula 1, Step 7. Conditions for deprotection of esters are well known in the art using a base such as sodium hydroxide or lithium hydroxide in a polar protic solvent such as ethanol or MeOH or a water/THF solvent mixture. Other alternative deprotection conditions include using trimethyltin hydroxide or potassium trimethylsilanolate as a base in dichloroethane or THF to give compounds of Formula I.

Scheme 2

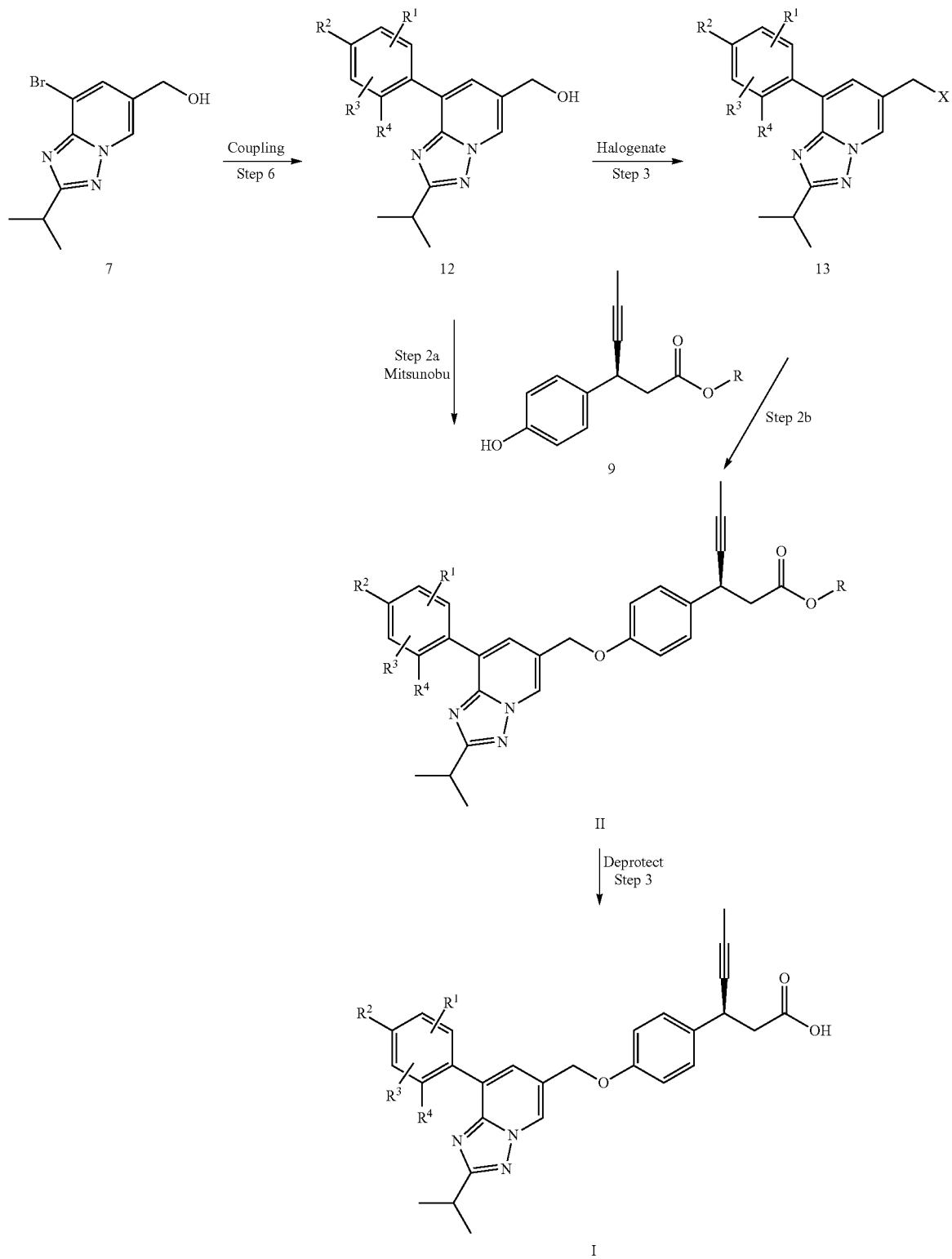

In another variation, shown in Scheme 2, the 8-bromo substituted [1,2,4]triazolo[1,5-a]pyridine (7, Step 1) can be coupled under Suzuki-Miyaura cross coupling conditions using a boronic acid reagent to give compound (12) as described in Scheme 1, Step 6. This alcohol (12) can then be reacted with a phenol (9) under Mitsunobu conditions as described above in Scheme 1, Step 5b, to give compound II in Step 2a. Alternatively, the alcohol of compound 12 can be halogenated to give compound 13 as described in Scheme 1, Step 4. The halogenated compound, (13) can then be alkylated under basic conditions as described in Scheme 1, Step 5b to give compound II, Step 2b. The compound of Formula II can then be deprotected as described for Scheme 1, Step 7 to give compounds of Formula I.

PREPARATIONS AND EXAMPLES

The following preparations and examples further illustrate the invention and represent typical synthesis of the compounds of Formula (I). Unless noted to the contrary, the compounds illustrated herein are named and numbered using Accelrys Draw 4.0, IUPACNAME ACDLABS or MDL ISIS, version 2.5 SP2.

Preparation 1

6-Amino-nicotinic acid methyl ester

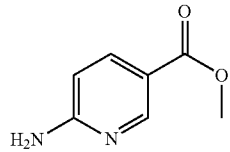

To a stirred solution of 6-amino-nicotinic acid (25 g, 181.1 mmol) in MeOH (200 mL) is added concentrated $H_2SO_4$ (7 mL) at 0° C. and the reaction mixture is heated at 80° C. for overnight. The reaction mixture is cooled to room temperature and neutralized with saturated $NaHCO_3$ solution (100 mL). The precipitated solid is filtered and dried under vacuum to give the title compound as a yellow solid (22 g, 81.5%). LCMS m/z 153 (M+H)$^+$.

Preparation 2

Ethyl 6-aminonicotinate

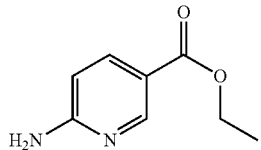

To a stirred solution of 6-aminonicotinic acid (3 Kg, 21.61 mol) in ethanol (30 L) is added concentrated $H_2SO_4$ (3 L) and the reaction mixture is heated at 78° C. for 16 hours. The reaction mixture is cooled to room temperature and evaporated under reduced pressure. The residue is neutralized to pH ~7.5 using saturated $NaHCO_3$ solution and extracted with EtOAc (3×5 L). The combined organic extracts are washed with water (2×5 L), brine solution (5 L), dried over sodium sulphate, and evaporated to give the title compound as an off white solid (3.4 Kg, 93.87%). LCMS m/z 167 (M+H)$^+$.

The following compound is prepared essentially by the method of preparation 2.

TABLE 1

| Prep. No. | Chemical Name | Structure | ES/MS (m/z) (M + 1) |
|---|---|---|---|
| 3 | 3-Bromo-2-methyl-benzoic acid ethyl ester | 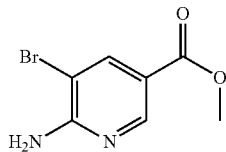 | 243/245 |

Preparation 4

6-Amino-5-bromo-nicotinic acid methyl ester

To a stirred solution of methyl 6-amino nicotinate (22 g, 143.7 mmol) in THF (500 mL) at 0° C. is added NBS (27.9 g, 158.1 mmol) and the reaction mixture is stirred at room temperature for overnight Ammonium chloride (100 mL) is added to the reaction mixture and the mixture is extracted with EtOAc (2×100 mL). The combined organic extracts are washed with brine solution (100 mL), dried over sodium sulphate, filtered, and evaporated under reduced pressure. The crude material is purified by silica gel column chromatography (combiflash) and eluted with 35% EtOAc in hexanes to give the title compound as a pale brown solid (28 g, 84.8%). LCMS m/z ($^{79}$Br/$^{81}$Br) 231/233 (M+H)$^+$.

The following compound is prepared essentially by the method of preparation 4.

TABLE 2

| Prep. No. | Chemical Name | Structure | ES/MS (m/z) (M + 1) |
|---|---|---|---|
| 5 | Ethyl 6-amino-5-bromonicotinate | 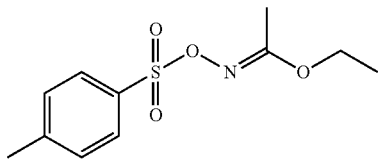 [SMILES: CCO/C(C)=N/OS(=O)(=O)c1ccc(C)cc1] | 245/247 |

Preparation 6

(E)-Ethyl N-(p-toluene sulfonyl) oxyacetimidate

To a stirred solution of (E)-ethyl N-hydroxyacetimidate (47.2 g, 458.7 mmol) in DMF (300 mL) is added triethylamine (128 mL, 917.4 mmol) at room temperature and the mixture is stirred for 20 minutes. p-Toluenesulphonyl chloride (100 g, 458.7 mmol) is added and the reaction mixture is stirred for 16 hours at room temperature. The reaction mixture is diluted with water (200 mL) and extracted with EtOAc (3×150 mL). The combined organic extracts are dried over sodium sulphate, filtered, and evaporated to give the title compound as a white solid (94 g, 80.3%). LCMS m/z 258 (M+H)+.

Preparation 7

(E)-Ethyl N-(mesitylsulfonyl)oxyacetimidate

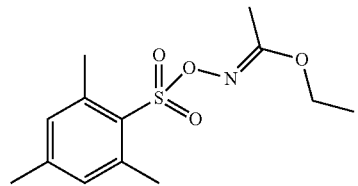 [SMILES: CCO/C(C)=N/OS(=O)(=O)c1c(C)cc(C)cc1C]

To a stirred solution of N-hydroxy-acetimidic acid ethyl ester (42 g, 183 mmol) in DMF (100 mL) is added triethylamine (49.2 mL, 366 mmol) at 0° C. The reaction mixture is stirred at room temperature for 10 minutes and cooled again to 0° C. 2,4,6-Trimethyl-benzenesulfonyl chloride (40 g, 183 mmol) is added portion wise. The reaction mixture is stirred overnight at room temperature. The reaction mixture is diluted with EtOAc (100 mL), washed with ice water (2×500 mL), brine solution (50 mL), dried over anhydrous sodium sulphate, filtered, and evaporated to give the title compound as a pale yellow solid (40 g, crude) that is used without further purification. LC-MS m/z 286.1 [M+H]+.

Preparation 8 tert-Butyl (mesitylsulfonyl)oxycarbamate

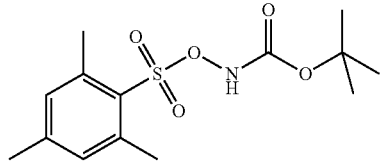 [SMILES: Cc1cc(C)c(S(=O)(=O)ONC(=O)OC(C)(C)C)c(C)c1]

To a stirred solution of 2,4,6-trimethylbenzene-1-sulfonyl chloride (5.5 Kg, 25.14 mol) in MTBE (55 L) is added tert-butyl hydroxycarbamate (4 Kg, 30.17 mol) and cooled to 0° C. Triethylamine (3.05 Kg, 30.17 mol) is added to the reaction mixture over a period of 1 hour and the reaction mixture is stirred at 0° C. for 2 hours. The reaction mixture is filtered and washed with MTBE (2×5 L). The filtrate is concentrated to a volume of 12 L and n-hexane (6 L) is added and the mixture is redistilled up to a volume of 12 L. To the crude compound 5% solution of MTBE in n-hexane (60 L) is added and the mixture is stirred for 2 hours. The reaction mixture is filtered to give the first crop as an off white solid compound (6.13 Kg). The filtrate is concentrated to dryness and 5% solution of MTBE in n-hexane (10 L) is added. The reaction mixture is stirred for 30 minutes and filtered to give a second crop of the title compound (0.86 Kg) which is combined with the first crop to give the title compound (6.99 g, 88%).

Preparation 9

O-(p-Toluene sulfonyl) hydroxylamine

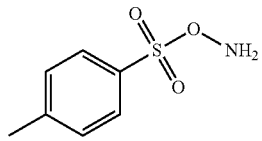

To a stirred solution of (E)-ethyl N-(p-toluene sulfonyl) oxyacetimidate (10 g, 38.9 mmol) in 1,4 dioxane (40 mL), HClO4 (3.0 mL) is added at 0° C. and the reaction mixture is stirred at room temperature for 1 hour. The reaction mixture is diluted with water and extracted with DCM (2×10 mL). The combined organic extracts are dried over sodium sulphate and filtered. The solution is used directly without concentration (9 g, 100% crude).

Preparation 10

O-(Mesitylsulfonyl) hydroxylamine

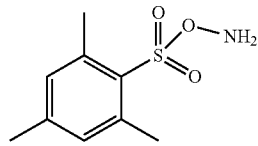

To a stirred solution of (E)-ethyl N-(mesitylsulfonyl) oxyacetimidate (16 g, 62.167 mmol) in 1,4-dioxane (200 mL) is added perchloric acid (8 mL) at 0° C. and the reaction mixture is stirred at room temperature for 1.5 hours. The reaction mixture is diluted with water (30 mL) and extracted with DCM (2×20 mL). The combined organic layer is washed with brine solution (20 mL), dried over anhydrous sodium sulphate, filtered and the filtrate is used without concentration.

Alternate Preparation 10

To a 100 L reactor containing trifluoroacetic acid (19.74 L) is added tert-butyl (mesitylsulfonyl)oxycarbamate (6.99 Kg, 22.18 mol) at 0° C. over a period of 45 minutes and the reaction mixture is stirred at 0° C. for 2 hours. The reaction mixture is quenched with crushed ice (8 L) followed by ice cold water (16 L) and stirred for 15 minutes. Additional ice cold water (24 L) is added and the mixture is stirred for 15 minutes. The solid precipitate is filtered, washed with water and dried to give a white solid which is used without further purification (4.77 Kg, 100%).

Preparation 11

1,2-Diamino-3-bromo-5-methoxycarbonyl-pyridinium 4-methylbenzenesulfonate

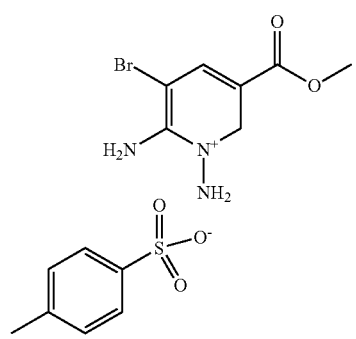

To a stirred solution of o-(p-toluene sulfonyl) hydroxylamine (9 g, 48.1 mmol) in DCM (50 mL) is added 6-amino-5-bromo-nicotinic acid methyl ester (11.1 g, 48.1 mmol) at room temperature and the mixture is stirred for 16 hours. The reaction mixture is cooled to 0° C. and diethyl ether is added. The precipitated solid is filtered and dried under vacuum to give the title compound as an off-white solid (9 g, 45%). $^1$H NMR (400 MHz, d$_6$-DMSO) δ 9.09 (bs, 2H), 8.69 (d, J=1.6 Hz, 1H), 8.46 (q, J=8.0 Hz, 1H), 7.06 (s, 3H), 6.71 (s, 2H), 4.31 (q, J=11.6 Hz, 2H), 2.14 (s, 3H), 1.25-1.32 (m, 4H).

The following compound is prepared essentially by the method of preparation 11.

Alternate Preparation 12

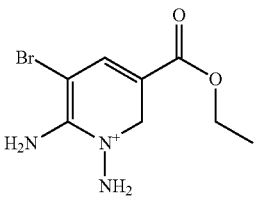

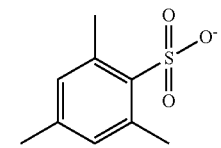

O-(Mesitylsulfonyl) hydroxylamine (assumed 4.77 Kg, 22.17 mol) as a wet cake is dissolved in DCM (25 L) and the aqueous layer is separated, the organic layer is washed with water (2×10 L) and brine solution (10 L). The organic layer is transferred to a 100 L reactor and diluted with additional DCM (45 L). The reaction mixture is cooled to 10° C.-15° C. and 6-amino-5-bromo-nicotinic acid ethyl ester (4.24 Kg, 17.29 mol) is added portion wise over a period of 15 minutes. The reaction mixture is stirred at room temperature for 16 hours. The reaction mixture is filtered and the solid cake is washed with DCM (3×10 L) and dried to give the first crop as a white solid (2.7 Kg). The filtrate is concentrated to give a thick mass which is triturated in DCM (20 L) for 2 hours. A solid is filtered and the wet cake is washed with DCM (2×5 L) and dried to give a second crop as an off white solid (1.1 Kg) which is combined with the first crop to give the title compound (3.8 Kg, 37.25%). LCMS m/z ($^{79}$Br/$^{81}$Br) 260/262 (M+H)$^+$.

TABLE 3

| Prep. No. | Chemical Name | Structure | NMR |
|---|---|---|---|
| 12 | 2,4,6-Trimethyl-benzenesulfonate 1,2-diamino-3-bromo-5-ethoxycarbonyl-pyridinium | 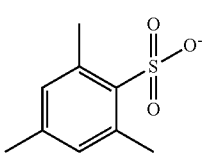 | a | a $^1$H NMR (400 MHz, d$_6$-DMSO) δ 9.09 (bs, 2H), 8.69 (d, J = 1.6 Hz, 1H), 8.46 (q, J = 8.0 Hz, 1H), 7.06 (s, 3H), 6.71 (s, 2H), 4.31 (q, J = 11.6 Hz, 2H), 2.14 (s, 3H), 1.25-1.32 (m, 4H).

Preparation 13

3-(4,4,5,5-Tetramethyl-[1,3,2]dioxaborolan-2-yl)-benzonitrile

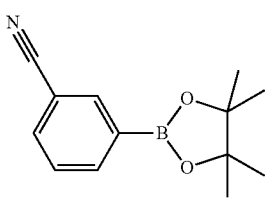 [SMILES: CC1(C)OB(c2cccc(C#N)c2)OC1(C)C]

To a stirred solution of 3-amino-benzonitrile (0.5 g, 4.23 mmol) in acetonitrile (30 mL) is added tert-butylnitrite (0.7 mL, 6.34 mmol) and bispinacolatodiboron (1.29 g, 5.076 mmol) at 0° C. The mixture is heated at 80° C. for 2 hours. The reaction mixture is cooled to room temperature and concentrated under reduced pressure. The crude material is purified by silica gel column chromatography (combiflash) eluting in 4% EtOAc/hexanes to obtain the title compound (0.35 g, 99.8%). LCMS m/z 294 (M+H)$^+$.

The following compound is prepared essentially by the method of preparation 13.

TABLE 4

| Prep. No. | Chemical Name | Structure | ES/MS (m/z) (M + 1) |
|---|---|---|---|
| 14 | 2-Methyl-2-[2-methyl-3-(4,4,5,5-tetramethyl-[1,3,2]dioxaborolan-2-yl)-phenyl]-propionitrile | 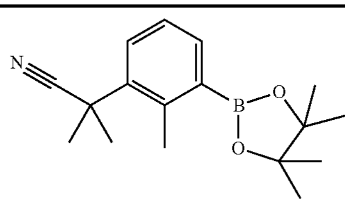 | 286 |

Preparation 15

3,5-Dimethyl-4-(4,4,5,5-tetramethyl-[1,3,2]dioxaborolan-2-yl)-benzonitrile

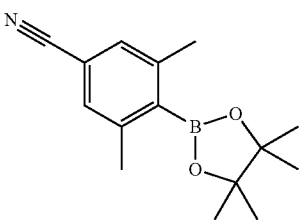 [SMILES: Cc1cc(C#N)cc(C)c1B1OC(C)(C)C(C)(C)O1]

To a stirred solution of 4-bromo-3,5-dimethyl-benzonitrile (0.5 g, 2.38 mmol) and bispinacolatodiboron (0.9 g, 3.57 mmol) in DMF (20 mL) is added CH$_3$COOK (1.051 g, 10.71 mmol). The mixture is purged with argon for 30 minutes, then Pd(dppf)$_2$Cl$_2$.DCM (0.097 g, 0.119 mmol) is added and the mixture is heated at 100° C. for overnight. The reaction mixture is cooled to room temperature and filtered through diatomaceous earth. The filtrate is diluted with water (30 mL) and extracted with EtOAc (2×30 mL). The combined organic extracts are washed with saturated brine solution (20 mL), dried over sodium sulphate, filtered, and concentrated. The crude material is purified by silica gel column chromatography (combiflash) eluting with 6% EtOAc/hexanes to obtain the title compound as a brown liquid (0.4 g, 65%). LCMS m/z 288 (M+H)$^+$.

Preparation 16

2-(4-Bromo-phenyl)-2-methyl-propionitrile

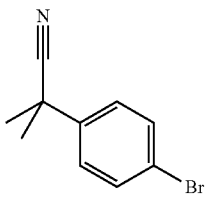

To a solution of (4-bromo-phenyl)-acetonitrile (1 g, 5.10 mmol) in DMF (10 mL) is added sodium hydride (0.408 g, 10.20 mmol, 60% in mineral oil) at 0° C. The reaction mixture is stirred at 0° C. for 15 minutes and then methyl iodide (0.69 mL, 11.22 mmol) is added at 0° C. The reaction mixture is stirred at room temperature for overnight. The reaction mixture is quenched with aqueous ammonium chloride solution (5 mL) and extracted with EtOAc (2×20 mL). The combined organic extracts are washed with water (20 mL) and brine (20 mL), dried over anhydrous Na$_2$SO$_4$, filtered, and evaporated. The crude material is purified over silica gel column chromatography (combiflash) eluting with 5-10% EtOAc in hexanes to give an off white solid (0.9 g, 78%). $^1$H NMR (400 MHz, CDCl$_3$) δ 7.51 (d, J=8.4 Hz, 1H), 7.34 (d, J=8.4 Hz, 1H), 1.77 (s, 3H).

The following compound is prepared essentially by the method of preparation 16.

TABLE 5

| Prep. No. | Chemical Name | Structure | ES/MS (m/z) (M + 1) |
|---|---|---|---|
| 17 | 2-(3-Bromo-phenyl)-2-methyl-propionitrile | 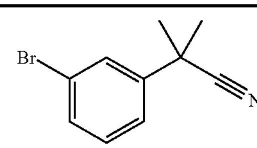 | 224/226 |

Preparation 18

4-Chloro-2,2-dimethylbutanenitrile

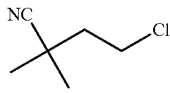

To a stirred solution of diisopropylamine (2.43 mL, 17.36 mmol) in dry THF (20 mL) is added n-BuLi (14.4 mL, 17.36 mmol) drop wise at −60° C., and gradually allowed to warm to 0° C. and stirred for 20 minutes. The reaction mixture is cooled to −78° C. and anhydrous acetonitrile (1.42 mL, 14.47 mmol) is added and the reaction is stirred for 45 minutes at the same temperature. 1-Bromo-4-chloro butane (1.3 mL, 15.91 mmol) is added at −78° C., allowed to warm to room temperature and stirred for 3 hours. The reaction mixture is quenched with saturated NH$_4$Cl solution (25 mL), extracted with EtOAc (2×50 mL). The combined organic extracts are washed with water (50 mL) and brine (50 mL), dried over anhydrous sodium sulphate, and evaporated to dryness. The crude product is purified by silica gel column chromatography (combiflash) eluting with 5% EtOAc in hexanes to give the title compound (0.5 g, 25.2%). $^1$H NMR (400 MHz, CDCl3); 3.67-3.63 (m, 2H), 2.06-2.02 (m, 2H), 1.45-1.36 (m, 6H).

Preparation 19

4-Bromo-2-methyl-butan-2-ol

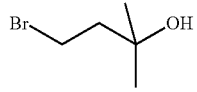

To a stirred solution of 4-bromo-butyric acid methyl ester (2 g, 12.27 mmol) in diethyl ether (20 mL) is added methyl magnesium bromide (16.4 mL, 49.08 mmol) at 0° C. and the mixture is stirred at room temperature for 2 hours. The reaction mixture is quenched with 1 N HCl and extracted with diethyl ether (2×20 mL). The combined organic extracts are washed with saturated brine solution (20 mL), dried over sodium sulphate, filtered, and concentrated. The crude material is purified with silica gel column chromatography (combiflash) eluting in 20% EtOAc/hexanes to give the title compound (1.3 g, 65%). $^1$H NMR (400 MHz, CDCl$_3$): δ 3.48 (t, J=8.0 Hz, 2H), 2.16 (t, J=7.4 Hz, 2H), 1.89 (s, 6H), 1.76 (s, 3H), 1.27 (s, 6H).

Preparation 20

8-Bromo-2-isopropyl-[1, 2, 4]triazolo[1,5-a]pyridine-6-carboxylic acid methyl ester

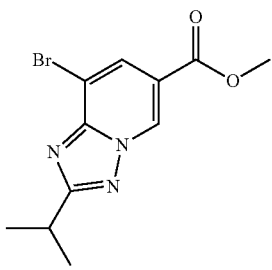 [SMILES: COC(=O)c1cc(Br)c2nc(C(C)C)nn2c1]

To a stirred solution of 1,2-diamino-3-bromo-5-methoxy-carbonyl-pyridinium 4-methyl benzenesulfonate (9 g, 21.4 mmol) in MeOH (35 mL) is added 2-methylpropanal (0.98 mL, 10.7 mmol) and triethylamine (8.6 mL, 64.2 mmol) at room temperature and the mixture is stirred for 48 hours. The reaction mixture is evaporated to dryness, the residue is diluted with water (50 mL), and extracted with EtOAc (2×50 mL). The combined organic extracts are washed with brine solution (50 mL), dried over sodium sulphate, filtered, and evaporated to dryness. The crude material is purified by silica gel column chromatography (combiflash) eluting with 15-20% EtOAc in hexane to give the title compound as a pale yellow solid (1.5 g, 12%). LCMS m/z ($^{79}$Br/$^{81}$Br) 298/300 (M+H)$^+$.

Alternate Preparation 20

To a stirred solution of 2,4,6-trimethyl-benzenesulfonate1,2-diamino-3-bromo-5-methoxy carbonyl-pyridinium (10 g, 22.3 mmol) in MeOH (100 mL) is added 2-methylpropanal (0.8 g, 1 mL, 11.1 mmol) and triethylamine (9 mL, 66.9 mmol) at 0° C. and the reaction mixture is stirred at room temperature for 48 hours. The reaction mixture is evaporated, diluted with water, and extracted with EtOAc (2×100 mL). The combined organic extracts are washed with water (2×50 mL), saturated ammonium chloride solution (50 mL), brine (50 mL), dried over anhydrous sodium sulphate, filtered, and evaporated to dryness. The crude material is purified by silica gel column chromatography (combiflash) eluting with 20-40% EtOAc in hexanes to give the title compound as an off white solid (2.7 g, 43.5%). LC-MS m/z ($^{79}$Br/$^{81}$Br) 298/300 [M+H]$^+$.

Preparation 21

8-Bromo-2-isopropyl-[1, 2, 4]triazolo[1,5-a]pyridine-6-carboxylic acid ethyl ester

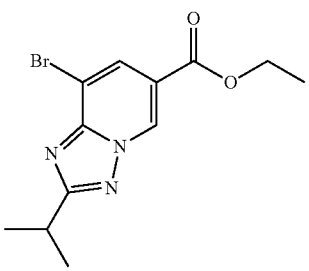 [SMILES: CCOC(=O)c1cc(Br)c2nc(C(C)C)nn2c1]

To a stirred solution of 1,2-diamino-3-bromo-5-(ethoxycarbonyl)pyridin-1-ium 2,4,6-trimethyl benzenesulfonate (2.2 Kg, 4.78 mol) in pyridine (6.6 L) is added 2-methylpropanoyl chloride (2.55 Kg, 23.90 mol) at room temperature and the reaction mixture is heated at 100° C. for 5 hours. The reaction mixture is evaporated to dryness, the residue is diluted with water (20 L), and stirred for 1 hour. The precipitated solid is filtered, washed with water (3×5 L) and dried. The crude product is purified by silica gel flash chromatography, eluting with hexanes: EtOAc (8.0:2.0) to give the title compound as an off white solid (800 g, 53.7%). LC-MS m/z ($^{79}$Br/$^{81}$Br) 312/314 [M+H]$^+$.

Preparation 22

(8-Bromo-2-isopropyl-[1,2,4]triazolo[1,5-a]pyridin-6-yl)-methanol

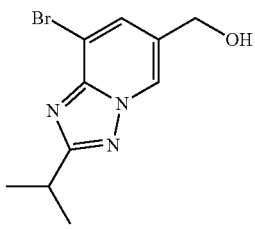

To a solution 8-bromo-2-isopropyl-[1,2,4]triazolo[1,5-a]pyridine-6-carboxylic acid methyl ester (1.4 g, 4.70 mmol) in DCM (30 mL) is added diisobutyl aluminum hydride (9.5 mL, 9 mmol, 1 M in hexane) at −78° C. The reaction mixture is warmed to 0° C. and stirred for 3 hours. The reaction mixture is quenched with MeOH (20 mL) and filtered through diatomaceous earth, washed with EtOAc (30 mL), and evaporated under reduced pressure to give the title product (1.8 g, 100% crude). LCMS m/z ($^{79}$Br/$^{81}$Br) 270/272 (M+H)$^+$.

The following compounds are prepared essentially by the method of preparation 22 using the appropriate carboxylic acid ester.

TABLE 6

| Prep. No. | Chemical Name | Structure | ES/MS (m/z) (M + 1) |
|---|---|---|---|
| 23 | (3-Bromo-2-methyl-phenyl)-methanol | 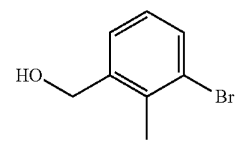 | 201/203 |
| 24 | [2-Isopropyl-8-(4-methoxy-2,6-dimethyl-phenyl)-[1,2,4]triazolo[1,5-a]pyridin-6-yl]-methanol | 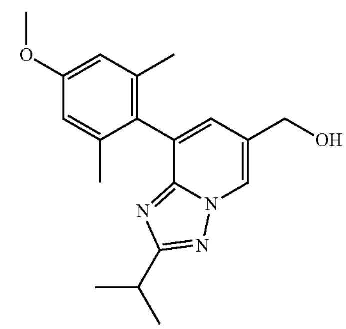 [SMILES: COc1cc(C)c(-c2cc(CO)cn3nc(C(C)C)nc23)c(C)c1] | 326 |
| 25 | {8-[4-(tert-Butyl-dimethyl-silanyloxy)-2,6-dimethyl-phenyl]-2-isopropyl-[1,2,4]triazolo[1,5-a]pyridin-6-yl}-methanol | 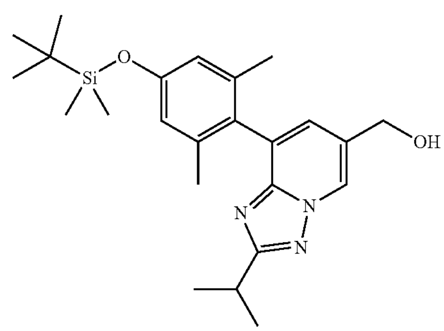 [SMILES: Cc1cc(O[Si](C)(C)C(C)(C)C)cc(C)c1-c1cc(CO)cn2nc(C(C)C)nc12] | 426 |
| 26 | [8-(2-Fluoro-5-methoxy-phenyl)-2-isopropyl-[1,2,4]triazolo[1,5-a]pyridin-6-yl]-methanol | 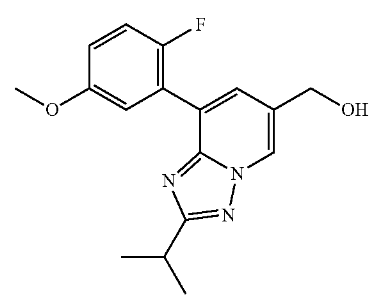 [SMILES: COc1ccc(F)c(-c2cc(CO)cn3nc(C(C)C)nc23)c1] | 316 |

TABLE 6-continued

| Prep. No. | Chemical Name | Structure | ES/MS (m/z) (M + 1) |
|---|---|---|---|
| 27 | (8-(2,6-Dimethyl-4-(3-(methylsulfonyl)propoxy)phenyl)-2-isopropyl-[1,2,4]triazolo[1,5-a]pyridin-6-yl) methanol | 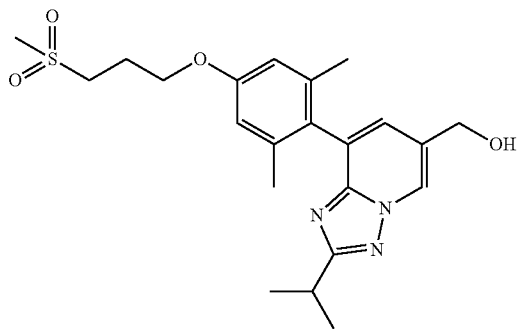 [SMILES: Cc1cc(OCCCS(C)(=O)=O)cc(C)c1-c1cc(CO)cn2nc(C(C)C)nc12] | 432 |
| 28 | [2-Isopropyl-8-(2-methoxy-ethoxy)-[1,2,4]triazolo[1,5-a]pyridin-6-yl]-methanol | 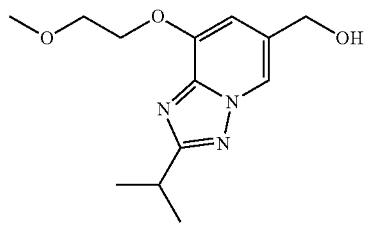 | 266 |

Preparation 29

8-Bromo-6-chloromethyl-2-isopropyl-[1,2,4]triazolo[1,5-a]pyridine

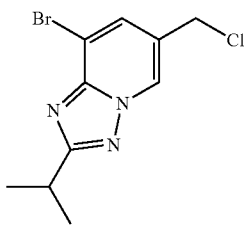

A mixture (8-bromo-2-isopropyl-[1,2,4]triazolo[1,5-a]pyridin-6-yl)-methanol (1.8 g, 0.57 mmol) and thionyl chloride (10 mL) is stirred at room temperature for 2 hours. The reaction mixture is quenched with saturated sodium bicarbonate solution (20 mL) and extracted with EtOAc (3×20 mL). The combined organic extracts are dried over sodium sulphate, filtered, and evaporated under vacuum to give the title compound (1.1 g, 67%). LCMS m/z ($^{79}$Br/$^{81}$Br) 288/290 [M+H]$^+$.

The following compounds are prepared essentially by the method of preparation 29.

TABLE 7

| Prep. No. | Chemical Name | Structure | ES/MS (m/z) (M + 1) |
|---|---|---|---|
| 30 | 6-Chloromethyl-8-(2-fluoro-5-methoxy-phenyl)-2-isopropyl-[1,2,4]triazolo[1,5-a]pyridine | 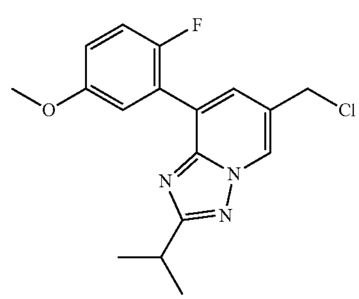 [SMILES: COc1ccc(F)c(-c2cc(CCl)cn3nc(C(C)C)nc23)c1] | 334 |

TABLE 7-continued

| Prep. No. | Chemical Name | Structure | ES/MS (m/z) (M + 1) |
|---|---|---|---|
| 31 | 6-(Chloromethyl)-8-(2,6-dimethyl-4-(3-(methylsulfonyl)propoxy)phenyl)-2-isopropyl-[1,2,4]triazolo[1,5-a]pyridine | 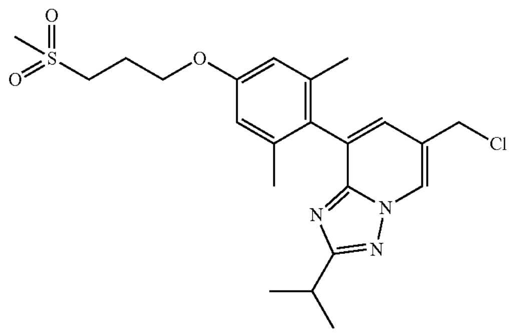 [SMILES: Cc1cc(OCCCS(C)(=O)=O)cc(C)c1-c1cc(CCl)cn2nc(C(C)C)nc12] | 450 |

Preparation 32

1-Bromo-3-bromomethyl-2-methyl-benzene

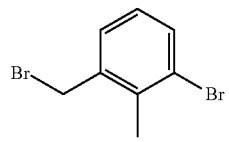

To a solution of (3-bromo-2-methyl-phenyl)-methanol (2 g, 9.9 mmol) in DCM (25 mL) is added phosphorous tribromide (1.76 mL, 14.9 mmol) at 0° C. and the reaction mixture is allowed to warm to room temperature and stirred 1 hour. The reaction mixture is diluted with DCM (20 mL), quenched with aqueous $NaHCO_3$ solution, and extracted with DCM (3×50 mL). The combined organic extracts are washed with water (10 mL) and brine (10 mL), dried over anhydrous $Na_2SO_4$, filtered, and evaporated to dryness to give the title compound (2 g, 77%). LC-MS m/z 264 $[M+H]^+$.

The following compounds are prepared essentially by the method of preparation 32.

TABLE 8

| Prep. No. | Chemical Name | Structure | ES/MS (m/z) (M + 1) |
|---|---|---|---|
| 33 | 6-Bromomethyl-2-isopropyl-8-(4-methoxy-2,6-dimethyl-phenyl)-[1,2,4]triazolo[1,5-a]pyridine | 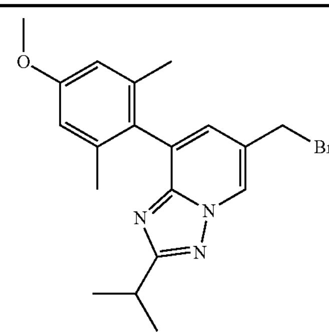 | 388/390 |
| 34 | 2-[2-(6-Bromomethyl-2-isopropyl-[1,2,4]triazolo[1,5-a]pyridin-8-yl)-phenyl]-2-methyl-propionitrile | 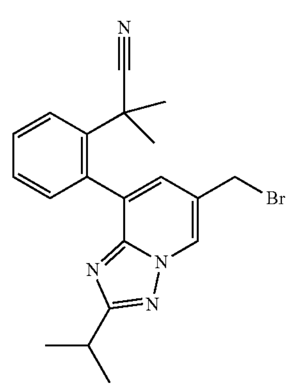 [SMILES: CC(C)c1nc2c(-c3ccccc3C(C)(C)C#N)cc(CBr)cn2n1] | 397/399 |

TABLE 8-continued

| Prep. No. | Chemical Name | Structure | ES/MS (m/z) (M + 1) |
|---|---|---|---|
| 35 | 6-Bromomethyl-2-isopropyl-8-[4-(2-methoxy-ethoxy)-2,6-dimethyl-phenyl]-[1,2,4]triazolo[1,5-a]pyridine | 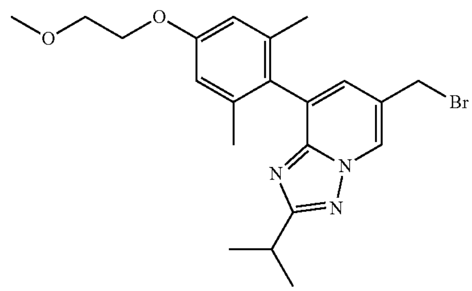 [SMILES: COCCOc1cc(C)c(-c2cc(CBr)cn3nc(C(C)C)nc23)c(C)c1] | 432/434 |

Preparation 36

(3-Bromo-2-methyl-phenyl)-acetonitrile

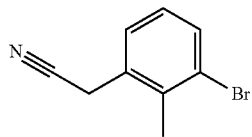

To a solution of bromo-3-bromomethyl-2-methyl-benzene (0.2 g, 7.6 mmol) in DMF (15 mL) is added sodium cyanide (0.55 g, 11.4 mmol) at room temperature. The reaction mixture is heated at 100° C. for 12 hours and quenched with potassium permanganate solution, filtered, and the filtrate is diluted with water and extracted with EtOAc (2×20 mL). The organic extracts are dried over Na$_2$SO$_4$, filtered, and evaporated. The crude material is purified over silica gel column chromatography (combiflash), eluting with EtOAc 10-25% in hexanes to give the title compound (0.8 g, 28.2%). LC-MS m/z 211 [M+H]$^+$.

Preparation 37

2-Isopropyl-8-(4-methoxy-2,6-dimethyl-phenyl)-[1,2,4]triazolo[1,5-a]pyridine-6-carboxylic acid methyl ester

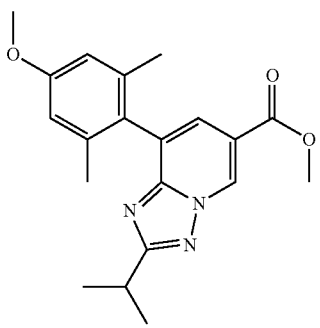 [SMILES: COC(=O)c1cc(-c2c(C)cc(OC)cc2C)c2nc(C(C)C)nn2c1]

To a stirred solution of 8-bromo-2-isopropyl-[1,2,4]triazolo[1,5-a]pyridine-6-carboxylic acid methyl ester (0.8 g, 2.6 mmol) and 4-methoxy 2,6-dimethyl phenyl boronic acid (0.522 g, 2.9 mmol) in toluene (12 mL) and EtOH (3 mL) is added 2 M K$_2$CO$_3$ solution (3.9 mL, 7.8 mmol). The mixture is purged with argon for 30 minutes, Pd(PPh$_3$)$_2$Cl$_2$ (0.182 g, 0.26 mmol) is added and the reaction mixture is heated at 100° C. for 16 hours. The reaction mixture is cooled to room temperature, filtered through diatomaceous earth, the filtrate is diluted with water (20 mL) and extracted with EtOAc (2×20 mL). The combined organic extracts are washed with saturated brine solution (10 mL), dried over sodium sulphate, filtered, and concentrated. The crude material is purified by silica gel column chromatography (combiflash) eluting with 15-20% EtOAc in hexanes to give the title compound as a yellow liquid (0.26 g, 27.4%). LCMS m/z 354 (M+H)$^+$.

Alternate Preparation 37

To a stirred solution of 8-bromo-2-isopropyl-[1,2,4]triazolo[1,5-a]pyridine-6-carboxylic acid methyl ester (2.5 g, 8.8 mmol) and 4-methoxy 2,6-dimethyl phenyl boronic acid (1.4 g, 8.83 mmol) in toluene (16 mL) is added potassium phosphate tribasic (5.3 g, 12.4 mmol) at room temperature and the reaction mixture is purged with nitrogen for 20 minutes and then added Pd(amphos)Cl$_2$ (0.57 g, 0.802 mmol). The reaction mixture is heated at 70° C. for overnight. The reaction mixture is filtered through diatomaceous earth, washed with EtOAc (2×20 mL) and the filtrate is evaporated. The crude material is purified by silica gel column chromatography (combiflash) eluting with 30% EtOAc in hexanes to give the title compound as a brown solid (1.5 g, 65.54%). LC-MS m/z 354 [M+H]$^+$.

Alternate Preparation 37

To a stirred solution of 8-bromo-2-isopropyl-[1,2,4]triazolo[1,5-a]pyridine-6-carboxylic acid methyl ester (1.05 g, 3.52 mmol) and 4-methoxy 2,6-dimethyl phenyl boronic acid (0.63 g, 3.52 mmol) in 1,4-dioxane (20 mL) is added 2 M K$_2$CO$_3$ solution (1.4 mL, 2.9 mmol). The mixture is purged with argon for 30 minutes, then Pd(PPh$_3$)$_2$Cl$_2$ (0.041 g, 0.059 mmol) is added and the reaction mixture is heated to 100° C. for 16 hours. The reaction mixture is cooled to room temperature, filtered through diatomaceous earth, the filtrate is diluted with water (20 mL) and extracted with EtOAc (2×20 mL). The combined organic extracts are washed with brine (10 mL), dried over sodium sulphate, filtered, and concentrated. The crude material is purified by silica gel column chromatography (combiflash) eluting with 14% EtOAc in hexanes to give the title compound (0.13 g, 16%). LCMS m/z 354 (M+H)+.

Preparation 38

2-Isopropyl-8-(4-methoxy-2,6-dimethyl-phenyl)-[1,2,4]triazolo[1,5-a]pyridine-6-carboxylic acid ethyl ester

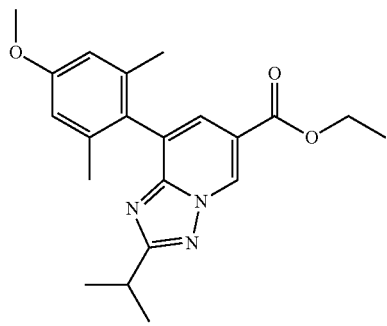 [SMILES: CCOC(=O)c1cc(-c2c(C)cc(OC)cc2C)c2nc(C(C)C)nn2c1]

To a stirred solution of 8-bromo-2-isopropyl-[1,2,4]triazolo[1,5-a]pyridine-6-carboxylic acid ethyl ester (400 g, 1.28 mol) and 4-methoxy 2,6-dimethylpheneyl boronic acid (276.8 g, 1.54 mol) in toluene (8 L) is added a solution of $K_3PO_4$ (816 g, 3.84 mol) in water (3.84 L) and the reaction mixture is purged with nitrogen for 1 hour, then Pd(amphos) $Cl_2$ (45.36 g, 0.064 mol) is added and the reaction mixture is purged with nitrogen for 20 minutes. The reaction mixture is heated at 75° C. for 16 hours. The reaction mixture is cooled to room temperature, filtered through diatomaceous earth, and washed with EtOAc (3×1 L). The filtrate is diluted with water (5 L) and extracted with EtOAc (2×1.5 L). The combined organic extracts are washed with water (2.5 L), brine (2.5 L), dried over sodium sulfate, filtered, and concentrated to dryness. The crude product (600 g) is combined with another crude lot (400 g) and purified on silica gel column chromatography eluting with 15-20% EtOAc in hexanes to give the title compound as a light yellow solid (901 g, 95.68%).

Preparation 39

8-(2-Fluoro-5-methoxy-phenyl)-2-isopropyl-[1,2,4]triazolo[1,5-a]pyridine-6-carboxylic acid ethyl ester

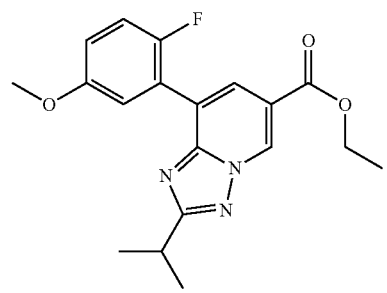 [SMILES: CCOC(=O)c1cc(-c2cc(OC)ccc2F)c2nc(C(C)C)nn2c1]

To a stirred solution of 8-bromo-2-isopropyl-[1,2,4]triazolo[1,5-a]pyridine-6-carboxylic acid ethyl ester (0.45 g, 1.509 mmol) and 2-flouro 4-methoxy phenyl boronic acid (0.512 g, 3.018 mmol) in 1,4-dioxane (6 mL) is added 2 M $K_2CO_3$ (0.624 g, 4.527 mmol). The mixture is purged with argon for 30 minutes, Pd(PPh$_3$)$_4$ (0.087 g, 0.075 mmol) is added and the mixture is heated at 100° C. for 1 hour in a microwave. The reaction mixture is cooled to room temperature and filtered through diatomaceous earth. The filtrate is diluted with water (20 mL) and extracted with EtOAc (2×10 mL). The combined organic layer is washed with brine (10 mL), dried over sodium sulphate, filtered, and concentrated. The crude material is purified by silica gel column chromatography (combiflash) eluting with 15-20% EtOAc in hexanes to give the title compound (0.17 g, 33%). LCMS m/z 344 (M+H)+.

Preparation 40

6-Chloromethyl-2-isopropyl-8-(4-methoxy-2,6-dimethyl-phenyl)-[1,2,4]triazolo[1,5-a]pyridine

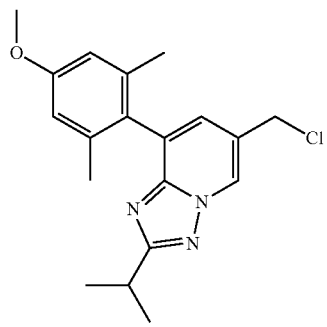 [SMILES: COc1cc(C)c(-c2cc(CCl)cn3nc(C(C)C)nc23)c(C)c1]

To a solution [2-isopropyl-8-(4-methoxy-2,6-dimethyl-phenyl)-[1,2,4]triazolo[1,5-a]pyridin-6-yl]-methanol (0.21 g, 0.64 mmol) in DCM (10 mL) is added $SOCl_2$ (0.12 mL, 1.61 mmol) at 0° C. Then the mixture is allowed to warm to room temperature over 1 hour. The reaction mixture is cooled to 0° C., quenched with saturated sodium bicarbonate solution (20 mL) and extracted with DCM (3×20 mL). The combined organic extracts are washed with brine solution, dried over sodium sulphate, filtered, and evaporated to dryness to give the title compound as a brown solid (0.06 g, 29%). LCMS m/z; 344 (M+H)+.

Preparation 41

2-[2-(6-Hydroxymethyl-2-isopropyl-[1,2,4]triazolo[1,5-a]pyridin-8-yl)-phenyl]-2-methyl-propionitrile

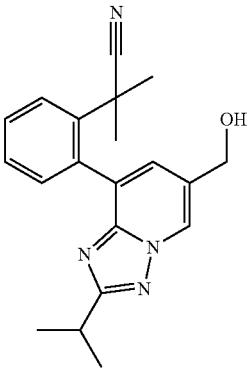 [SMILES: CC(C)c1nc2c(-c3ccccc3C(C)(C)C#N)cc(CO)cn2n1]

To a stirred solution of 2-{2-[6-(tert-butyl-dimethyl-silanyloxymethyl)-2-isopropyl-[1,2,4]triazolo[1,5-a]pyridin-8-yl]-phenyl}-2-methyl-propionitrile (0.6 g, 1.33 mmol) in THF (10 mL) is added tetra-n-butyl ammonium fluoride (0.52 g, 2 mmol) at 0° C. and the reaction mixture is stirred at room temperature for 1 hour. The reaction mixture is diluted with water (10 mL) and extracted with EtOAc (2×20 mL). The combined organic extracts are washed with water (10 mL) and brine (10 mL), dried over anhydrous sodium sulphate, filtered, and evaporated to dryness. The crude material is purified by silica gel column chromatography (combiflash), eluting with 40% EtOAc in hexanes to give the title compound as a white solid (0.4 mg, 50%). LC-MS m/z 335 [M+H]$^+$.

Preparation 42

8-Bromo-6-(tert-butyl-dimethyl-silanyloxymethyl)-2-isopropyl-[1,2,4]triazolo[1,5-a]pyridine

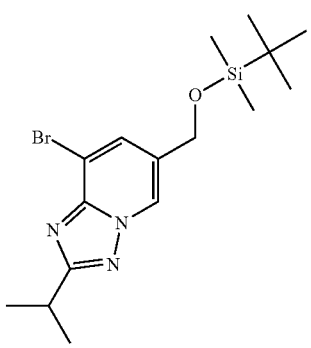 [SMILES: CC(C)c1nc2c(Br)cc(CO[Si](C)(C)C(C)(C)C)cn2n1]

To a stirred solution of 8-bromo-2-isopropyl-[1,2,4]triazolo[1,5-a]pyridin-6-yl)-methanol (0.25 g, 0.92 mmol) in DMF (5 mL) at 0° C. is added imidazole (0.209 g, 1.38 mmol) and the reaction mixture is stirred at room temperature for 5 minutes, cooled to 0° C. and tert-butylchlorodimethylsilane (0.209 g, 1.38 mmol) is added. The reaction mixture is stirred at room temperature for 12 hours. The reaction mixture is diluted water and extracted with EtOAc (2×25 mL). The combined organic extracts are washed with brine (20 mL), dried over Na$_2$SO$_4$, filtered, and evaporated to dryness. The crude product is purified by silica gel column chromatography (combiflash) eluting with 10-30% EtOAc in hexanes to give the title compound (0.32 g, 90%). LCMS m/z 384/386 [M+H]$^+$.

Preparation 43

{2-[6-(tert-Butyl-dimethyl-silanyloxymethyl)-2-isopropyl-[1,2,4]triazolo[1,5-a]pyridin-8-yl]-phenyl}-acetonitrile

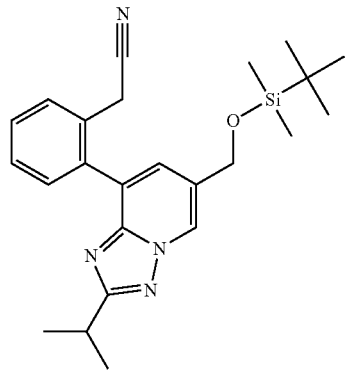 [SMILES: CC(C)c1nc2c(-c3ccccc3CC#N)cc(CO[Si](C)(C)C(C)(C)C)cn2n1]

To a stirred solution of 8-bromo-6-(tert-butyl-dimethyl-silanyloxymethyl)-2-isopropyl-[1,2,4]triazolo[1,5-a]pyridine (1.3 g, 3.38 mmol) and [2-(4,4,5,5-tetramethyl-[1,3,2]dioxaborolan-2-yl)-phenyl]-acetonitrile (0.82 g, 3.38 mmol) in dioxane (10 mL) is added potassium acetate (0.93 g, 6.76 mmol) at room temperature and the reaction mixture is purged with nitrogen for 20 minutes. Pd(PPh$_3$)$_4$ (0.195 g, 0.16 mmol) is added and the reaction mixture is heated at 100° C. for 12 hours in a sealed tube. The reaction mixture is cooled and filtered through diatomaceous earth and the filtrate is evaporated to dryness. The crude product is purified by silica gel column chromatography (combiflash) eluting with 10-30% EtOAc in hexanes to give the title compound (0.6 g, 42%). LCMS m/z 421 [M+H]$^+$.

Preparation 44

2-(3-Bromo-2-methyl-phenyl)-2-methyl-propionitrile

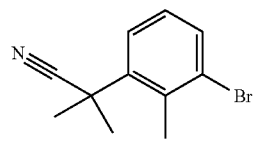

To a solution of NaH (0.22 g, 5.6 mmol, 60% in paraffin oil) in THF at 0° C. is added a solution of (3-bromo-2-methyl-phenyl)-acetonitrile (0.6 g, 2.8 mmol) in THF (4 mL). The reaction mixture is stirred at room temperature for 30 minutes and then methyl iodide (0.43 mL, 7 mmol) is added. The reaction mixture is stirred at room temperature for 12 hours, quenched with saturated aqueous NH$_4$Cl solution, and extracted in EtOAc (2×25 mL). The organic layer is washed with brine (10 mL), dried over Na$_2$SO$_4$, filtered, and evaporated. The crude of another lot (1 g) is combined with this lot and purified over silica gel column chromatography (combiflash), eluting with 10-30% EtOAc in hexanes to give the title compound (1.2 g, 75.9%). LC-MS m/z 239 [M+H]$^+$.

The following compounds are prepared essentially by the method of Preparation 44.

TABLE 9

| Prep. No. | Chemical Name | Structure | LC/MS (m/z) (M + 1) |
|---|---|---|---|
| 45 | 2-{2-[6-(tert-Butyl-dimethyl-silanyloxymethyl)-2-isopropyl-[1,2,4]triazolo[1,5-a]pyridin-8-yl]-phenyl}-propionitrile | 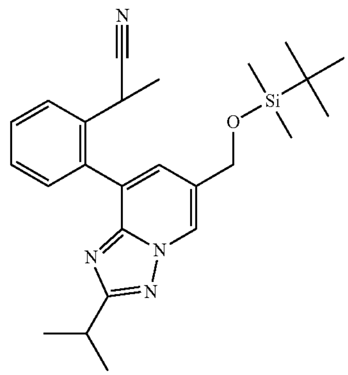 [SMILES: CC(C)c1nc2c(-c3ccccc3C(C)C#N)cc(CO[Si](C)(C)C(C)(C)C)cn2n1] | 435 |
| 46 | 2-{2-[6-(tert-Butyl-dimethyl-silanyloxymethyl)-2-isopropyl-[1,2,4]triazolo[1,5-a]pyridin-8-yl]-phenyl}-2-methyl-propionitrile | 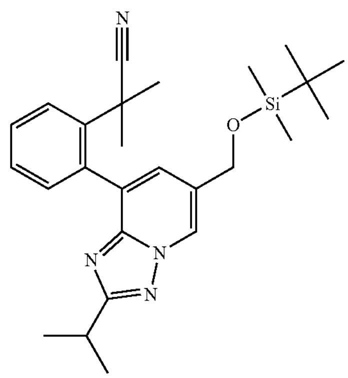 [SMILES: CC(C)c1nc2c(-c3ccccc3C(C)(C)C#N)cc(CO[Si](C)(C)C(C)(C)C)cn2n1] | 449 |

Preparation 47

2-Isopropyl-8-(4-methoxy-2,6-dimethyl-phenyl)-[1,2,4]triazolo[1,5-a]pyridine-6-carboxylic acid methyl ester

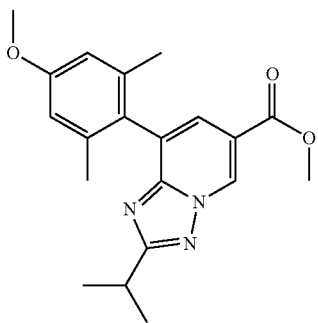 [SMILES: COC(=O)c1cc(-c2c(C)cc(OC)cc2C)c2nc(C(C)C)nn2c1]

To a stirred solution of 8-bromo-2-isopropyl-[1,2,4]triazolo[1,5-a]pyridine-6-carboxylic acid methyl ester (0.8 g, 2.6 mmol) and 4-methoxy 2,6-dimethyl phenyl boronic acid (0.522 g, 2.9 mmol) in toluene (12 mL) and EtOH (3 mL) is added 2 M $K_2CO_3$ solution (3.9 mL, 7.8 mmol). The mixture is purged with argon for 30 minutes, $Pd(PPh_3)_2Cl_2$ (0.182 g, 0.26 mmol) is added and the reaction mixture is heated at 100° C. for 16 hours. The reaction mixture is cooled to room temperature, filtered through diatomaceous earth, the filtrate is diluted with water (20 mL) and extracted with EtOAc (2×20 mL). The combined organic extracts are washed with saturated brine solution (10 mL), dried over sodium sulphate, filtered, and concentrated. The crude material is purified by silica gel column chromatography (combiflash) eluting with 15-20% EtOAc in hexanes to give the title compound as a yellow liquid (0.26 g, 27.4%). LCMS m/z 354 (M+H)$^+$.

Alternate Preparation 47

To a stirred solution of 8-bromo-2-isopropyl-[1,2,4]triazolo[1,5-a]pyridine-6-carboxylic acid methyl ester (2.5 g, 8.8 mmol) and 4-methoxy 2,6-dimethyl phenyl boronic acid (1.4 g, 8.83 mmol) in toluene (16 mL) is added potassium phosphate tribasic (5.3 g, 12.4 mmol) at room temperature and the reaction mixture is purged with nitrogen for 20 minutes and then $Pd(amphos)Cl_2$ (0.57 g, 0.802 mmol) is added. The reaction mixture is heated at 70° C. for overnight. The reaction mixture is filtered through diatomaceous earth, washed with EtOAc (2×20 mL) and the filtrate is evaporated. The crude material is purified by silica gel column chromatography (combiflash) eluting with 30% EtOAc in hexanes to give the title compound as a brown solid (1.5 g, 65.54%). LC-MS m/z 354 [M+H]$^+$.

Alternate Preparation 47

To a stirred solution of 8-bromo-2-isopropyl-[1,2,4]triazolo[1,5-a]pyridine-6-carboxylic acid methyl ester (1.05 g, 3.52 mmol) and 4-methoxy 2,6-dimethyl phenyl boronic acid (0.63 g, 3.52 mmol) in 1,4-dioxane (20 mL) is added 2 M $K_2CO_3$ solution (1.4 mL, 2.9 mmol). The mixture is purged with argon for 30 minutes, then $Pd(PPh_3)_2Cl_2$ (0.041 g, 0.059 mmol) is added and the reaction mixture is heated at 100° C. for 16 hours. The reaction mixture is cooled to room temperature, filtered through diatomaceous earth, the filtrate is diluted with water (20 mL) and extracted with EtOAc (2×20 mL). The combined organic extracts are washed with brine (10 mL), dried over sodium sulphate, filtered, and concentrated. The crude material is purified by silica gel column chromatography (combiflash) eluting with 14% EtOAc in hexanes to give the title compound (0.13 g, 16%). LCMS m/z 354 (M+H)+.

Preparation 48

2-Isopropyl-8-(4-methoxy-2,6-dimethyl-phenyl)-[1,2,4]triazolo[1,5-a]pyridine-6-carboxylic acid ethyl ester

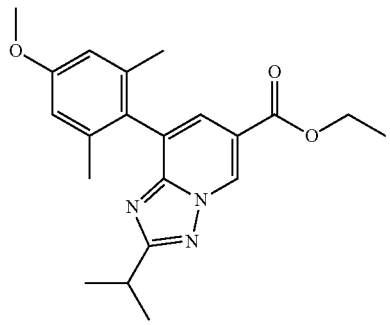 [SMILES: CCOC(=O)c1cc(-c2c(C)cc(OC)cc2C)c2nc(C(C)C)nn2c1]

To a stirred solution of 8-bromo-2-isopropyl-[1,2,4]triazolo[1,5-a]pyridine-6-carboxylic acid ethyl ester (400 g, 1.281 mol) and 4-methoxy 2,6-dimethylpheneyl boronic acid (276.8 g, 1.538 mol) in toluene (8 L) is added a solution of $K_3PO_4$ (816 g, 3.844 mol) in water (3.84 L) and the reaction mixture is purged with nitrogen for 1 hour, then Pd(amphos)Cl$_2$ (45.36 g, 0.064 mol) is added and the reaction mixture is purged with nitrogen for 20 minutes. The reaction mixture is heated at 75° C. for 16 hours. The reaction mixture is cooled to room temperature, filtered through diatomaceous earth, and washed with EtOAc (3×1 L). The filtrate is diluted with water (5 L) and extracted with EtOAc (2×1.5 L). The combined organic extracts are washed with water (2.5 L), brine (2.5 L), dried over sodium sulfate, filtered, and concentrated to dryness. The crude product (600 g) is combined with another crude lot (400 g) and purified on silica gel column chromatography eluting with 15-20% EtOAc in hexanes to give the title compound as a light yellow solid (901 g, 95.68%).

Preparation 49

8-Bromo-2-isopropyl-[1, 2, 4]triazolo[1,5-a]pyridine-6-carboxylic acid methyl ester

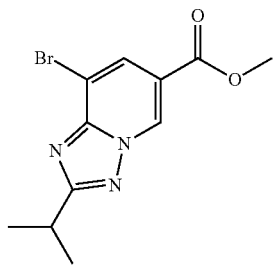 [SMILES: COC(=O)c1cc(Br)c2nc(C(C)C)nn2c1]

To a stirred solution of 1,2-diamino-3-bromo-5-methoxycarbonyl-pyridinium 4-methyl benzenesulfonate (9 g, 21.4 mmol) in MeOH (35 mL) is added isobutyraldehyde (0.98 mL, 10.7 mmol) and triethylamine (8.6 mL, 64.2 mmol) at room temperature and the mixture is stirred for 48 hours. The reaction mixture is evaporated to dryness, the residue is diluted with water (50 mL), and extracted with EtOAc (2×50 mL). The combined organic extracts are washed with brine solution (50 mL), dried over sodium sulphate, filtered, and evaporated to dryness. The crude material is purified by silica gel column chromatography (combiflash) eluting with 15-20% EtOAc in hexanes to give the title compound as a pale yellow solid (1.5 g, 12%). LCMS m/z ($^{79}$Br/$^{81}$Br) 298/300 (M+H)+.

Alternate Preparation 49

To a stirred solution of 2,4,6-trimethyl-benzenesulfonate1,2-diamino-3-bromo-5-methoxy carbonyl-pyridinium (10 g, 22.3 mmol) in MeOH (100 mL) is added 2-methyl-propionaldehyde (0.8 g, 1 mL, 11.1 mmol) and triethylamine (9 mL, 66.9 mmol) at 0° C. and the reaction mixture is stirred at room temperature for 48 hours. The reaction mixture is evaporated, diluted with water, and extracted with EtOAc (2×100 mL). The combined organic extracts are washed with water (2×50 mL), saturated ammonium chloride solution (50 mL), brine (50 mL), dried over anhydrous sodium sulphate, filtered, and evaporated to dryness. The crude material is purified by silica gel column chromatography (combiflash) eluting with 20-40% EtOAc in hexanes to give the title compound as an off white solid (2.7 g, 43.5%). LC-MS m/z ($^{79}$Br/$^{81}$Br) 298/300 [M+H]+.

Preparation 50

8-Bromo-2-isopropyl-[1, 2, 4]triazolo[1,5-a]pyridine-6-carboxylic acid ethyl ester

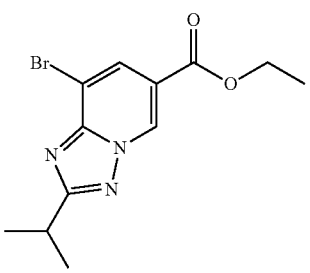 [SMILES: CCOC(=O)c1cc(Br)c2nc(C(C)C)nn2c1]

To a stirred solution of 1,2-diamino-3-bromo-5-(ethoxycarbonyl)pyridin-1-ium 2,4,6-trimethyl benzenesulfonate (2.2 Kg, 4.779 mol) in pyridine (6.6 L) is added isobutyryl chloride (2.546 Kg, 23.895 mol) at room temperature and the reaction mixture is heated at 100° C. for 5 hours. The reaction mixture is evaporated to dryness, the residue is diluted with water (20 L), and stirred for 1 hour. The precipitated solid is filtered, washed with water (3×5 L) and dried. The crude product is purified by silica gel flash chromatography, eluting with hexane: EtOAc (8.0:2.0) to give the title compound as an off white solid (800 g, 53.7%). LC-MS m/z ($^{79}$Br/$^{81}$Br) 312/314 [M+H]+.

Preparation 51

(8-Bromo-2-isopropyl-[1,2,4]triazolo[1,5-a]pyridin-6-yl)-methanol

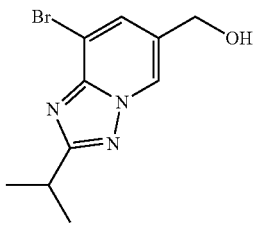

To a solution 8-bromo-2-isopropyl-[1,2,4]triazolo[1,5-a]pyridine-6-carboxylic acid methyl ester (1.4 g, 4.70 mmol) in DCM (30 mL) is added diisobutyl aluminum hydride (9.5 mL, 9 mmol, 1 M in hexane) at −78° C. The reaction mixture is warmed to 0° C. and stirred for 3 hours. The reaction mixture is quenched with MeOH (20 mL) and filtered through diatomaceous earth, washed with EtOAc (30 mL), and evaporated under reduced pressure to give the title product (1.8 g, 100% crude). LCMS m/z ($^{79}$Br/$^{81}$Br) 270/272 (M+H)$^+$.

The following compounds are prepared essentially by the method of preparation 51.

TABLE 10

| Prep. No. | Chemical Name | Structure | ES/MS (m/z) (M + 1) |
|---|---|---|---|
| 52 | (3-Bromo-2-methyl-phenyl)-methanol | 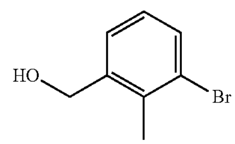 | 201/203 |
| 53 | [2-Isopropyl-8-(4-methoxy-2,6-dimethyl-phenyl)-[1,2,4]triazolo[1,5-a]pyridin-6-yl]-methanol | 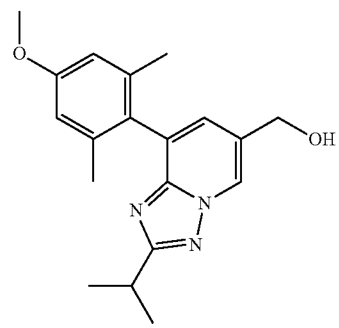 [SMILES: COc1cc(C)c(-c2cc(CO)cn3nc(C(C)C)nc23)c(C)c1] | 326 |
| 54 | {8-[4-(tert-Butyl-dimethyl-silanyloxy)-2,6-dimethyl-phenyl]-2-isopropyl-[1,2,4]triazolo[1,5-a]pyridin-6-yl}-methanol | 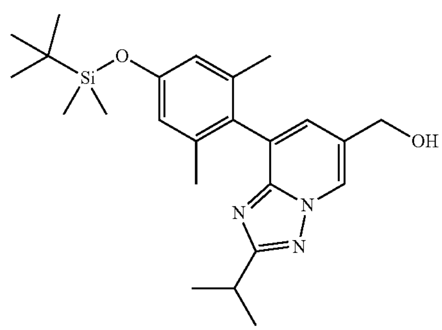 [SMILES: Cc1cc(O[Si](C)(C)C(C)(C)C)cc(C)c1-c1cc(CO)cn2nc(C(C)C)nc12] | 426 |
| 55 | [8-(2-Fluoro-5-methoxy-phenyl)-2-isopropyl-[1,2,4]triazolo[1,5-a]pyridin-6-yl]-methanol | 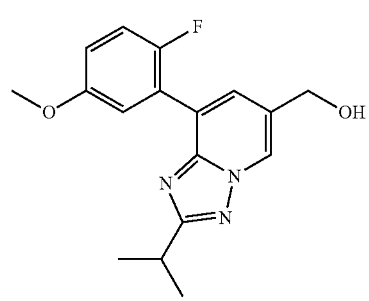 [SMILES: COc1ccc(F)c(-c2cc(CO)cn3nc(C(C)C)nc23)c1] | 316 |

TABLE 10-continued

| Prep. No. | Chemical Name | Structure | ES/MS (m/z) (M + 1) |
|---|---|---|---|
| 56 | (8-(2,6-Dimethyl-4-(3-(methylsulfonyl)propoxy)phenyl)-2-isopropyl-[1,2,4]triazolo[1,5-a]pyridin-6-yl) methanol | 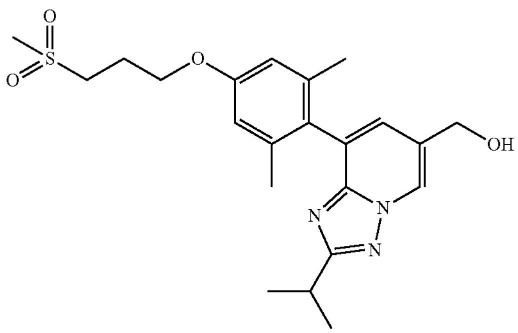 [SMILES: Cc1cc(OCCCS(C)(=O)=O)cc(C)c1-c1cc(CO)cn2nc(C(C)C)nc12] | 432 |
| 57 | [2-Isopropyl-8-(2-methoxy-ethoxy)-[1,2,4]triazolo[1,5-a]pyridin-6-yl]-methanol | 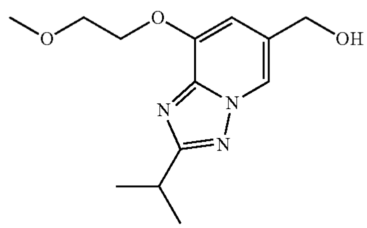 [SMILES: COCCOc1cc(CO)cn2nc(C(C)C)nc12] | 266 |

Preparation 58

8-Bromo-6-chloromethyl-2-isopropyl-[1,2,4]triazolo[1,5-a]pyridine

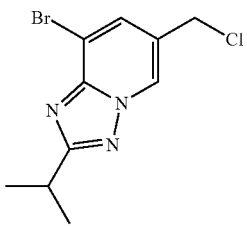

A mixture (8-bromo-2-isopropyl-[1,2,4]triazolo[1,5-a]pyridin-6-yl)-methanol (1.8 g, 0.57 mmol) and thionyl chloride (10 mL) is stirred at room temperature for 2 hours. The reaction mixture is quenched with saturated sodium bicarbonate solution (20 mL) and extracted with EtOAc (3×20 mL). The combined organic extracts are dried over sodium sulphate, filtered, and evaporated under vacuum to give the title compound (1.1 g, 67%). LCMS m/z ($^{79}$Br/$^{81}$Br) 288/290 [M+H]$^+$.

The following compounds are prepared essentially by the method of preparation 58.

TABLE 11

| Prep. No. | Chemical Name | Structure | ES/MS (m/z) (M + 1) |
|---|---|---|---|
| 59 | 6-Chloromethyl-8-(2-fluoro-5-methoxy-phenyl)-2-isopropyl-[1,2,4]triazolo[1,5-a]pyridine | 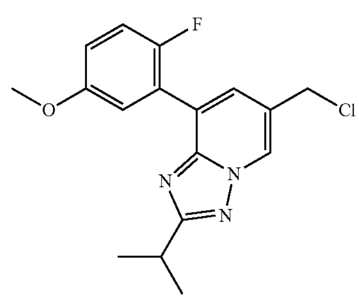 [SMILES: COc1ccc(F)c(-c2cc(CCl)cn3nc(C(C)C)nc23)c1] | 334 |

TABLE 11-continued

| Prep. No. | Chemical Name | Structure | ES/MS (m/z) (M + 1) |
|---|---|---|---|
| 60 | 6-(Chloromethyl)-8-(2,6-dimethyl-4-(3-(methylsulfonyl)propoxy)phenyl)-2-isopropyl-[1,2,4]triazolo[1,5-a]pyridine | 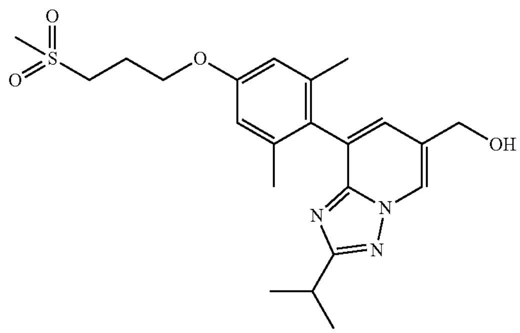 [SMILES: Cc1cc(OCCCS(C)(=O)=O)cc(C)c1-c1cc(CO)cn2nc(C(C)C)nc12] | 450 |

Preparation 61

(S)-3-[4-(8-Bromo-2-isopropyl-[1,2,4]triazolo[1,5-a]pyridin-6-ylmethoxy)-phenyl]-hex-4-ynoic acid ethyl ester

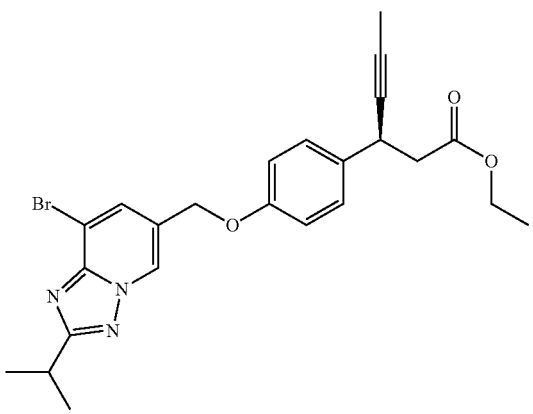 [SMILES: CC#C[C@@H](CC(=O)OCC)c1ccc(OCc2cc(Br)c3nc(C(C)C)nn3c2)cc1]

To a stirred solution of (S)-3-(4-hydroxy-phenyl)-hex-4-ynoic acid ethyl ester (1.1 g, 3.8 mmol) and 8-bromo-6-chloromethyl-2-isopropyl-[1,2,4]triazolo[1,5-a]pyridine in acetonitrile (20 mL) is added cesium carbonate (2.48 g, 7.62 mmol). The reaction mixture is stirred overnight at room temperature. The reaction mixture is filtered through diatomaceous earth, washed with EtOAc (20 mL) and evaporated to dryness. The residue is dissolved in EtOAc (30 mL), washed with water (2×30 mL) and brine solution (20 mL), dried over sodium sulphate, and evaporated under reduced pressure. The crude material is purified by silica gel column chromatography (combiflash), eluting with 35-40% EtOAc in hexanes to give the title compound (1.0 g, 53.4%). LCMS m/z ($^{79}$Br/$^{81}$Br) 484/486 (M+H)$^+$.

The following compounds are prepared essentially by the method of preparation 61.

TABLE 12

| Prep. No. | Chemical Name | Structure | ES/MS (m/z) (M + 1) |
|---|---|---|---|
| 62 | S)-3-{4-[2-Isopropyl-8-(4-methoxy-2,6-dimethyl-phenyl)-[1,2,4]triazolo[1,5-a]pyridin-6-ylmethoxy]-phenyl}-hex-4-ynoic acid ethyl ester | 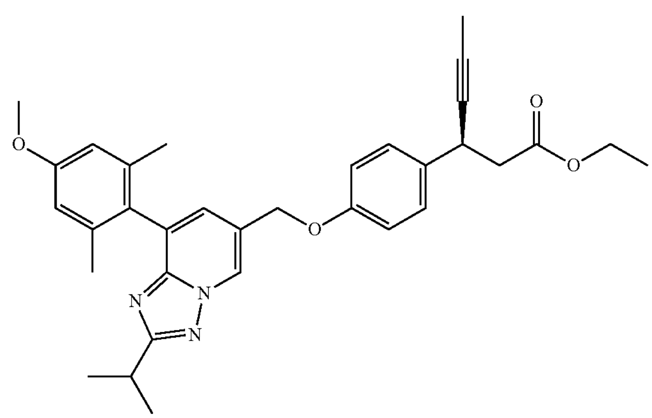 [SMILES: CC#C[C@@H](CC(=O)OCC)c1ccc(OCc2cc(-c3c(C)cc(OC)cc3C)c3nc(C(C)C)nn3c2)cc1] | 540 |

TABLE 12-continued

| Prep. No. | Chemical Name | Structure | ES/MS (m/z) (M + 1) |
|---|---|---|---|
| 63 | (S)-3-(4-{8-[2-(Cyano-dimethyl-methyl)-phenyl]-2-isopropyl-[1,2,4]triazolo[1,5-a]pyridin-6-ylmethoxy}-phenyl)-hex-4-ynoic acid ethyl ester | 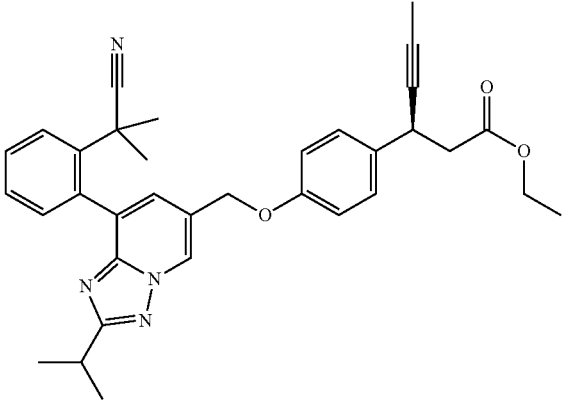 [SMILES: CC#C[C@@H](CC(=O)OCC)c1ccc(OCc2cc(-c3ccccc3C(C)(C)C#N)c3nc(C(C)C)nn3c2)cc1] | 549 |
| 64 | (S)-3-{4-[8-(2-Fluoro-5-methoxy-phenyl)-2-isopropyl-[1,2,4]triazolo[1,5-a]pyridin-6-ylmethoxy]-phenyl}-hex-4-ynoic acid ethyl ester | 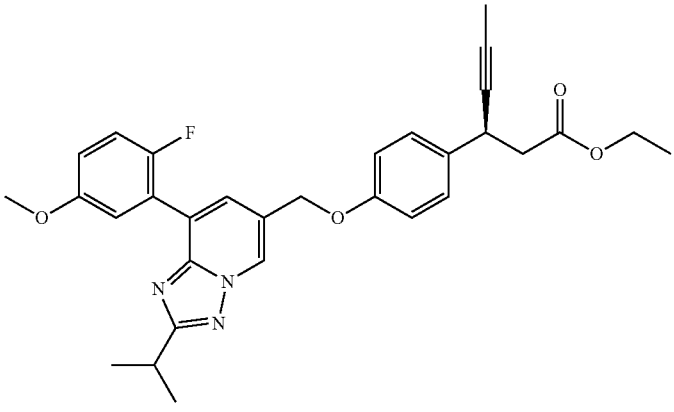 [SMILES: CC#C[C@@H](CC(=O)OCC)c1ccc(OCc2cc(-c3cc(OC)ccc3F)c3nc(C(C)C)nn3c2)cc1] | 530 |
| 65 | (S)-Ethyl 3-(4-((8-(2,6-dimethyl-4-(3-(methylsulfonyl)propoxy)phenyl)-2-isopropyl-[1,2,4]triazolo[1,5-a]pyridin-6-yl)methoxy)phenyl)hex-4-ynoate | 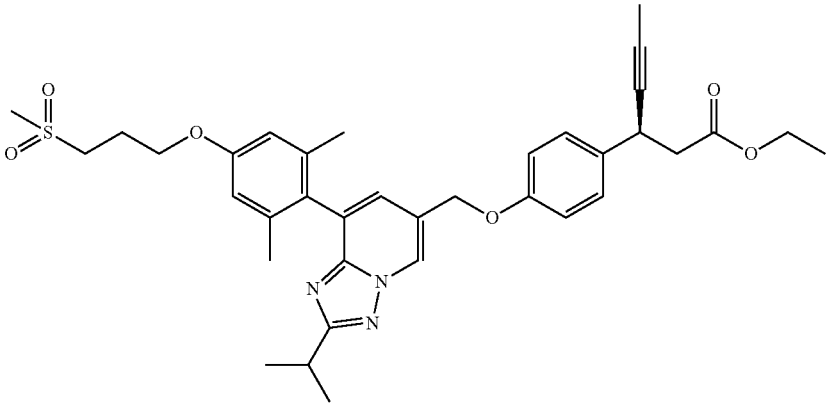 [SMILES: CC#C[C@@H](CC(=O)OCC)c1ccc(OCc2cc(-c3c(C)cc(OCCCS(C)(=O)=O)cc3C)c3nc(C(C)C)nn3c2)cc1] | 646 |

TABLE 12-continued

| Prep. No. | Chemical Name | Structure | ES/MS (m/z) (M + 1) |
|---|---|---|---|
| 66 | (S)-3-(4-{2-Isopropyl-8-[4-(2-methoxy-ethoxy)-2,6-dimethyl-phenyl]-[1,2,4]triazolo[1,5-a]pyridin-6-ylmethoxy}-phenyl)-hex-4-ynoic acid ethyl ester | 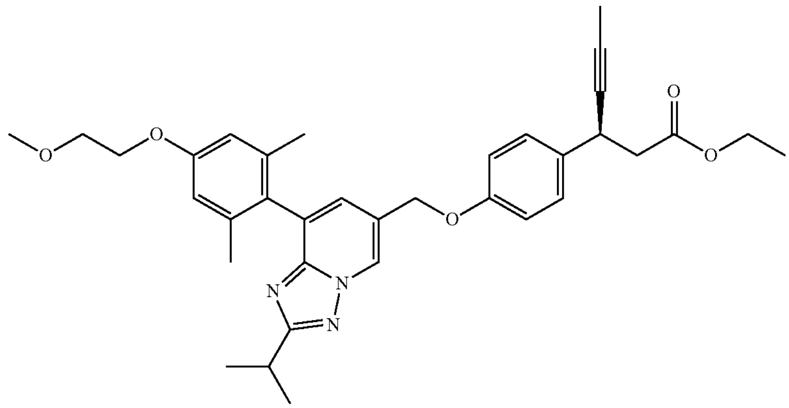 [SMILES: CC#C[C@@H](CC(=O)OCC)c1ccc(OCc2cc(-c3c(C)cc(OCCOC)cc3C)c3nc(C(C)C)nn3c2)cc1] | 584 |

Preparation 67

(S)-3-{4-[8-(4-Cyano-phenyl)-2-isopropyl-[1,2,4]triazolo[1,5-a]pyridin-6-ylmethoxy]-phenyl}-hex-4-ynoic acid ethyl ester

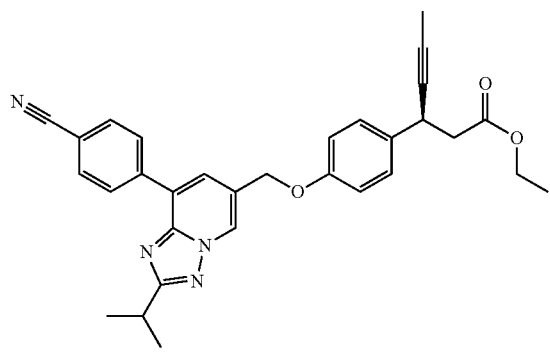 [SMILES: CC#C[C@@H](CC(=O)OCC)c1ccc(OCc2cc(-c3ccc(C#N)cc3)c3nc(C(C)C)nn3c2)cc1]

To a stirred solution of (S)-3-[4-(8-bromo-2-isopropyl-[1,2,4]triazolo[1,5-a]pyridin-6-ylmethoxy)-phenyl]-hex-4-ynoic acid ethyl ester (1.0 g, 2.07 mmol) and 4-cynophenylboronic acid (0.602 g, 9.6 mmol) in 1,4 dioxane (10 mL) is added a solution of 2 M potassium carbonate (0.542 g, 6.18 mmol). The mixture is purged under nitrogen atmosphere for 20 minutes and Pd(PPh$_3$)$_4$ (0.117 g, 0.103 mmol) is added. The reaction mixture is stirred at 100° C. in a microwave for 4 hours. The reaction mixture is diluted with EtOAc (30 mL), washed with water (2×30 mL) and brine solution (30 mL), dried over anhydrous sodium sulphate, filtered, and evaporated under reduced pressure. The residue is purified by silica gel column chromatography (combi-flash) eluting with 30-40% EtOAc in hexanes to give the title compound as a colorless liquid (0.500 g, 47.8%). LCMS m/z 507 (M−H)$^+$.

The following compounds are prepared essentially by the method of preparation 67.

TABLE 13

| Prep. No. | Chemical Name | Structure | ES/MS (m/z) (M + 1) |
|---|---|---|---|
| 68 | (S)-3-{4-[8-(2-Cyanomethyl-phenyl)-2-isopropyl-[1,2,4]triazolo[1,5-a]pyridin-6-ylmethoxy]-phenyl}-hex-4-ynoic acid ethyl ester | 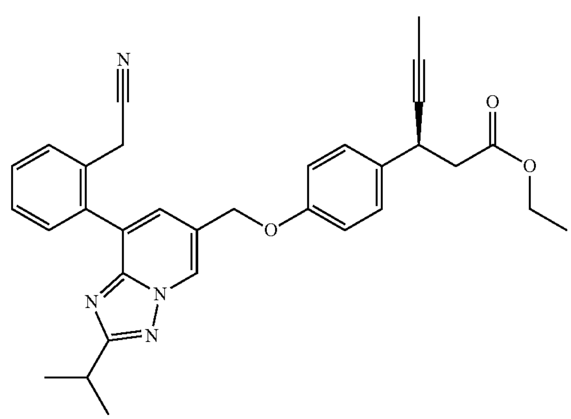 [SMILES: CC#C[C@@H](CC(=O)OCC)c1ccc(OCc2cc(-c3ccccc3CC#N)c3nc(C(C)C)nn3c2)cc1] | 521 |

TABLE 13-continued
| Prep. No. | Chemical Name | Structure | ES/MS (m/z) (M + 1) |
|---|---|---|---|
| 69 | (S)-3-{4-[8-(2,6-Dimethyl-phenyl)-2-isopropyl-[1,2,4]triazolo[1,5-a]pyridin-6-ylmethoxy]-phenyl}-hex-4-ynoic acid ethyl ester | 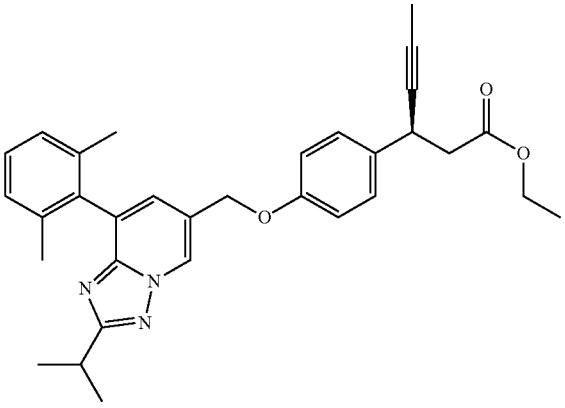 [SMILES: CC#C[C@@H](CC(=O)OCC)c1ccc(OCc2cc(-c3c(C)cccc3C)c3nc(C(C)C)nn3c2)cc1] | 510 |
| 70 | (S)-3-{4-[8-(4-Cyano-2,6-dimethyl-phenyl)-2-isopropyl-[1,2,4]triazolo[1,5-a]pyridin-6-ylmethoxy]-phenyl}-hex-4-ynoic acid ethyl ester | 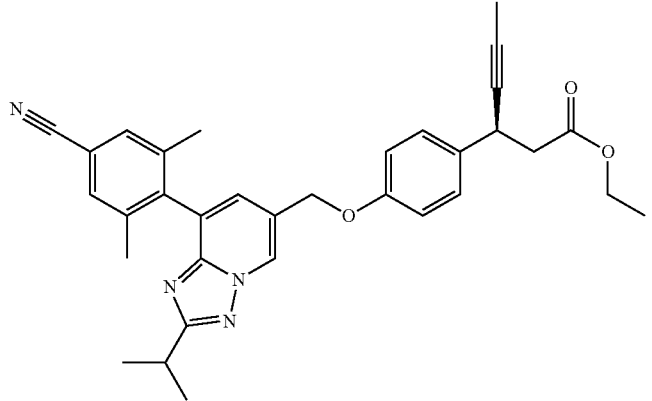 [SMILES: CC#C[C@@H](CC(=O)OCC)c1ccc(OCc2cc(-c3c(C)cc(C#N)cc3C)c3nc(C(C)C)nn3c2)cc1] | 535 |
| 71 | (S)-3-{4-[8-(3-Cyano-phenyl)-2-isopropyl[1,2,4]triazolo[1,5-a]pyridin-6-ylmethoxy]-phenyl}-hex-4-ynoic acid ethyl ester | 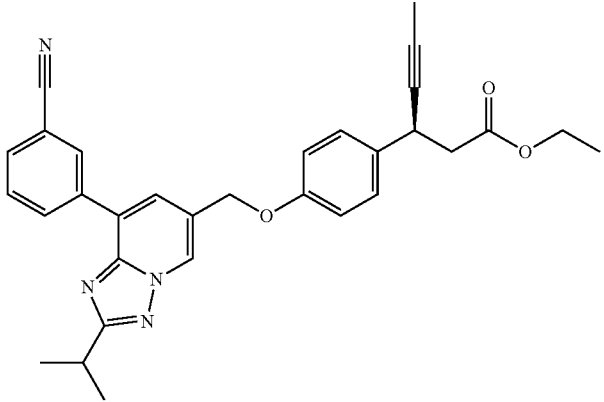 [SMILES: CC#C[C@@H](CC(=O)OCC)c1ccc(OCc2cc(-c3cccc(C#N)c3)c3nc(C(C)C)nn3c2)cc1] | 507 |

Preparation 72

(S)-3-(4-{8-[4-(Cyano-dimethyl-methyl)-phenyl]-2-isopropyl-[1,2,4]triazolo[1,5-a]pyridin-6-yl-methoxy}-phenyl)-hex-4-ynoic acid ethyl ester

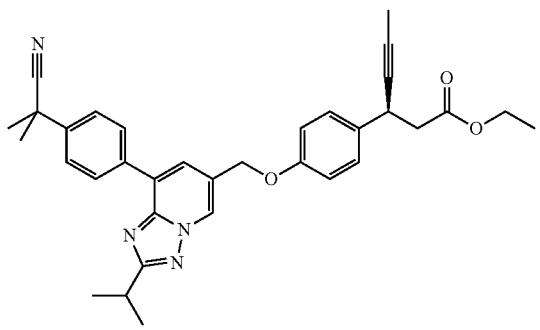 [SMILES: CC#C[C@@H](CC(=O)OCC)c1ccc(OCc2cc(-c3ccc(C(C)(C)C#N)cc3)c3nc(C(C)C)nn3c2)cc1]

To a stirred solution of 2-methyl-2-[4-(4,4,5,5-tetramethyl-[1,3,2]dioxaborolan-2-yl)-phenyl]-propionitrile (0.184 g, 0.680 mmol) and (S)-3-[4-(8-bromo-2-isopropyl-[1,2,4]triazolo[1,5-a]pyridine-6-ylmethoxy)-phenyl]-hex-4-ynoic acid ethyl ester (0.3 g, 0.619 mmol) in 1,4-dioxane (10 mL) is added 2 M potassium carbonate (0.619 mL, 1.238 mmol) at room temperature. The reaction mixture is purged under a nitrogen atmosphere for 20 minutes and Pd(PPh$_3$)$_2$Cl$_2$ (0.021 g, 0.0309 mmol) is added. The reaction mixture is heated at 100° C. for 16 hours. The reaction mixture is filtered through diatomaceous earth and washed with EtOAc (2×20 mL). The filtrate is washed with cold water (2×10 mL), brine solution (10 mL), dried over anhydrous sodium sulphate, filtered, and evaporated to dryness. The crude material is purified on silica gel column chromatography (combiflash), eluting with 30-50% EtOAc in hexanes to give the title compound as a colorless liquid (0.13 g, 38%). LC-MS m/z 547 [M+H]$^+$.

The following compound is prepared essentially by the method of preparation 72.

Preparation 74

(S)-3-{4-[8-(2-Cyano-phenyl)-2-isopropyl-[1,2,4]triazolo[1,5-a]pyridin-6-ylmethoxy]-phenyl}-hex-4-ynoic acid ethyl ester

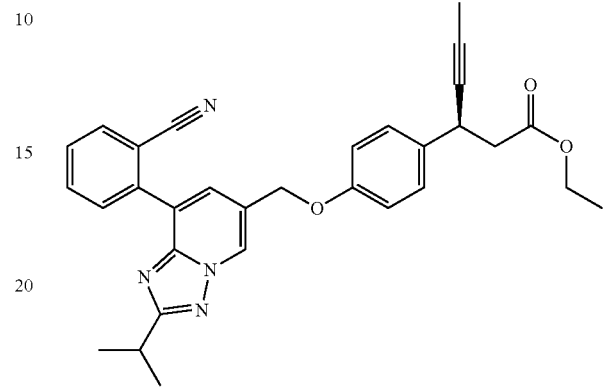

To a stirred solution (S)-3-[4-[8-(8-bromo-2-isopropyl-[1,2,4]triazolo[1,5-a]pyridin-6-ylmethoxy]-phenyl}-hex-4-ynoic acid ethyl ester (0.200 g, 1.64 mmol) and 2-(4,4,5,5-tetramethyl-[1,3,2]dioxaborolan-2-yl)-benzonitrile (0.110 g, 1.96 mmol) in 1,4 dioxane (9 mL) is added solid potassium carbonate (0.172 g, 4.92 mmol). The mixture is purged under a nitrogen atmosphere for 20 minutes and Pd(PPh$_3$)$_4$ (0.024 g, 0.800 mmol) is added. The reaction mixture is heated at 100° C. for overnight, filtered through diatomaceous earth, washed with EtOAc, and evaporated under reduced pressure to dryness. The residue is purified by silica gel column chromatography (combiflash) eluting with 29-32% EtOAc in hexanes to give the title compound. (0.140 g, 66%). LCMS m/z 507 (M+H)$^+$.

TABLE 14

| Prep. No. | Chemical Name | Structure | ES/MS (m/z) (M + 1) |
|---|---|---|---|
| 73 | (S)-3-{4-[8-(3-Cyanomethyl-phenyl)-2-isopropyl-[1,2,4]triazolo[1,5-a]pyridin-6-ylmethoxy]-phenyl}-hex-4-ynoic acid ethyl ester | 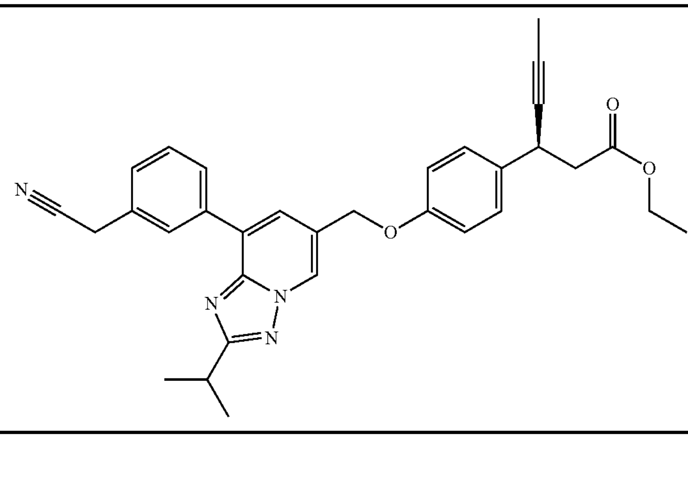 | 521 |

Preparation 75

(S)-3-(4-{8-[3-(Cyano-dimethyl-methyl)-phenyl]-2-isopropyl-[1,2,4]triazolo[1,5-a]pyridin-6-yl-methoxy}-phenyl)-hex-4-ynoic acid ethyl ester

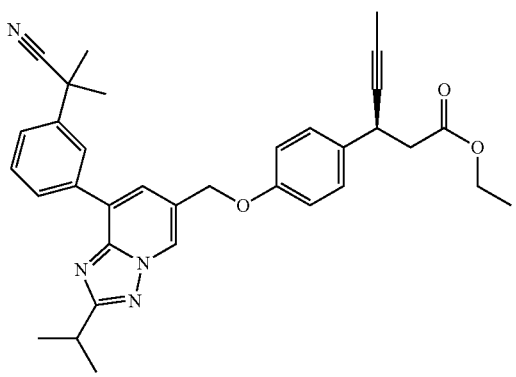 [SMILES: CC#C[C@@H](CC(=O)OCC)c1ccc(OCc2cc(-c3cccc(C(C)(C)C#N)c3)c3nc(C(C)C)nn3c2)cc1]

To a stirred solution of (S)-3-[4-(8-bromo-2-isopropyl-[1,2,4]triazolo[1,5-a]pyridin-6-ylmethoxy)-phenyl]-hex-4-ynoic acid ethyl ester (0.4 g, 0.82 mmol) and 2-methyl-2-[3-(4,4,5,5-tetramethyl-[1,3,2]dioxaborolan-2-yl)-phenyl]-propionitrile (0.23 g, 0.9 mmol) in 1,4-dioxane (40 mL) is added K$_2$CO$_3$ (0.33 g, 2.4 mmol). The mixture is purged with nitrogen for 10 minutes. Then Pd(dppf)$_2$Cl$_2$.DCM (0.066 g, 0.08 mmol) is added and the mixture is heated at 100° C. for 12 hours. The reaction mixture is cooled to room temperature and filtered through diatomaceous earth. The filtrate is washed with EtOAc (2×30 mL), dried over anhydrous sodium sulphate, filtered, and concentrated. The crude material is purified on silica gel column chromatography (combiflash), eluting with 15-20% EtOAc in hexanes to give the title compound (0.1 g, 22.22%). LCMS m/z 549.5 (M+H)$^+$.

Preparation 76

8-(4-Hydroxy-2,6-dimethyl-pheny)-2-isopropyl-[1,2,4]triazolo[1,5-a]pyridine-6-carboxylic acid methyl ester

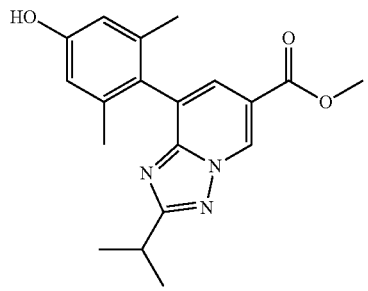 [SMILES: COC(=O)c1cc(-c2c(C)cc(O)cc2C)c2nc(C(C)C)nn2c1]

To a solution of 2-isopropyl-8-(4-methoxy-2,6-dimethyl-phenyl)-[1,2,4]triazolo[1,5-a]pyridine-6-carboxylic acid methyl ester (1.25 g, 3.5 mmol) in DCM (30 mL) is added borontribromide (0.51 mL, 5.3 mmol) at −40° C. The reaction mixture is stirred at room temperature for 1 hour. The reaction mixture is quenched with aqueous sodium bicarbonate solution (5 mL) and extracted with EtOAc (2×20 mL). The combined organic extracts are washed with water (10 mL) and brine solution (10 mL), dried over anhydrous sodium sulphate, filtered, and evaporated to give the title compound (0.9 g, 76%). LC-MS m/z 340 [M+H]$^+$.

Preparation 77

8-[4-(tert-Butyl-dimethyl-silanyloxy)-2,6-dimethyl-phenyl]-2-isopropyl-[1,2,4]triazolo[1,5-a]pyridine-6-carboxylic acid methyl ester

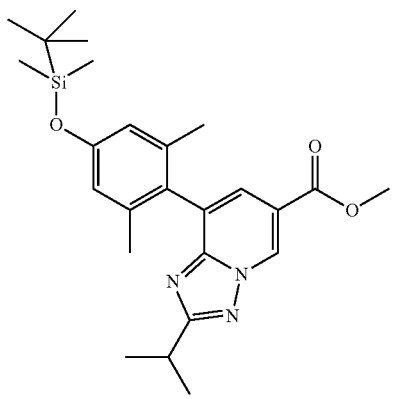 [SMILES: COC(=O)c1cc(-c2c(C)cc(O[Si](C)(C)C(C)(C)C)cc2C)c2nc(C(C)C)nn2c1]

To a stirred solution of 8-(4-hydroxy-2,6-dimethyl-phenyl)-2-isopropyl-[1,2,4]triazolo[1,5-a]pyridine-6-carboxylic acid methyl ester (0.9 g, 2.65 mmol) in DMF (30 mL) is added imidazole (0.540 g, 7.96 mmol) and tert-butyldimethylchlorosilane (1.2 g, 7.96 mmol) at 0° C. The reaction mixture is stirred at room temperature for 16 hours. The reaction mixture is diluted with water (30 mL) and extracted with EtOAc (2×50 mL). The combined organic extracts are washed with water (30 mL) and brine solution (30 mL), dried over anhydrous sodium sulphate, filtered, and evaporated. The crude material is purified by silica gel column chromatography (combiflash), eluting with 8% EtOAc in hexanes to give the title compound (1.1 g, 92%). LC-MS m/z 454 [M+H]$^+$.

Preparation 78

((S)-3-(4-{8-[4-(tert-Butyl-dimethyl-silanyloxy)-2,6-dimethyl-phenyl]-2-isopropyl[1,2,4]triazolo[1,5-a]pyridin-6-ylmethoxy}-phenyl)-hex-4-ynoic acid ethyl ester

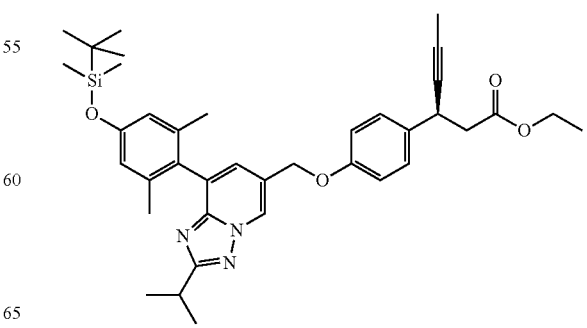

To a stirred solution of {8-[4-(tert-butyl-dimethyl-silanyloxy)-2,6-dimethyl-phenyl]-2-isopropyl-[1,2,4]triazolo[1,5-a]pyridin-6-yl}-methanol (0.8 g, 1.8 mmol) in DCM (20 mL) is added (S)-3-(4-hydroxy-phenyl)-hex-4-ynoic acid ethyl ester (0.655 g, 2.8 mmol), DEAD (0.43 mL, 2.8 mmol), and triphenylphosphine (0.566 g, 2.16 mmol). The reaction mixture is stirred at room temperature for 90 minutes. The reaction mixture is evaporated and the crude material is purified by silica gel column chromatography (combiflash), eluting with 18% EtOAc in hexanes to give the title compound (1 g, 91%). LC-MS m/z 640 [M+H]$^+$.

Preparation 79

(S)-3-{4-[8-(4-Hydroxy-2,6-dimethyl-phenyl)-2-isopropyl-[1,2,4]triazolo[1,5-a]pyridin-6-yl-methoxy]-phenyl}-hex-4-ynoic acid ethyl ester

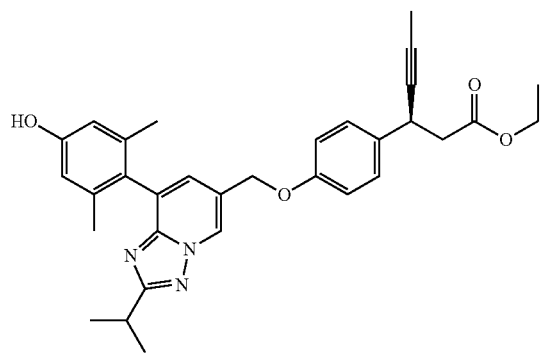 [SMILES: CC#C[C@@H](CC(=O)OCC)c1ccc(OCc2cc(-c3c(C)cc(O)cc3C)c3nc(C(C)C)nn3c2)cc1]

To a stirred solution of (S)-3-(4-{8-[4-(tert-butyl-dimethyl-silanyloxy)-2,6-dimethyl-phenyl]-2-isopropyl-[1,2,4]triazolo[1,5-a]pyridin-6-ylmethoxy}-phenyl)-hex-4-ynoic acid methyl ester (0.1 g, 1.56 mmol) in THF (20 mL) is added tetra-n-butyl ammonium fluoride (0.8 g, 3.12 mmol) at 0° C. The reaction mixture is stirred at room temperature for 1 hour. The mixture is diluted with water (10 mL) and extracted with EtOAc (2×20 mL). The combined organic extracts are washed with water (10 mL) and brine (10 mL), dried over anhydrous sodium sulphate, filtered, and evaporated to dryness. The crude material is purified by silica gel column chromatography (combiflash), eluting with 40% EtOAc in hexanes to give the title compound as a white solid (0.4 g, 50%). LC-MS m/z 526 [M+H]$^+$.

Preparation 80

2-Isopropyl-8-[4-(2-methoxy-ethoxy)-2,6-dimethyl-phenyl]-[1,2,4]triazolo[1,5-a]pyridine-6-carboxylic acid methyl ester

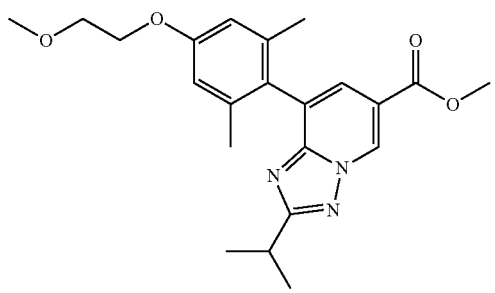

To a stirred solution of 8-(4-hydroxy-2,6-dimethyl-phenyl)-2-isopropyl-[1,2,4]triazolo[1,5-a]pyridine-6-carboxylic acid methyl ester (0.40 g, 1.185 mmol) and 1-bromo-2-methoxy-ethane (0.82 mL, 9.06 mmol) in acetonitrile (15 mL) is added cesium carbonate (0.734 g, 2.26 mmol) at room temperature. The reaction mixture is stirred at room temperature overnight. The mixture is filtered through diatomaceous earth, washed with EtOAc (20 mL), and concentrated to give a residue. The residue is dissolved in EtOAc (30 mL), washed with water (2×30 mL), brine solution (30 mL), dried over sodium sulphate, filtered, and evaporated under reduced pressure. The crude compound is purified with silica gel column chromatography (combiflash), eluting with 30% EtOAc in hexanes to give the title compound as a white semi solid (0.350 g, 87%). LCMS m/z 397 (M+H)$^+$.

Preparation 81

Ethyl 8-(2,6-dimethyl-4-(3-(methylsulfonyl)propoxy)phenyl)-2-isopropyl-[1,2,4]triazolo[1,5-a]pyridine-6-carboxylate

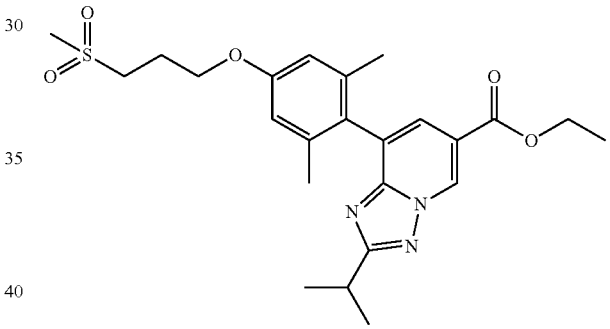

To a stirred solution of ethyl 8-(4-hydroxy-2,6-dimethylphenyl)-2-isopropyl-[1,2,4]triazolo[1,5-a]pyridine-6-carboxylate (1.1 g, 3.11 mmol) and 3-(methylsulfonyl)propyl-4-methylbenzenesulfonate (1.09 g, 3.73 mmol) in DMF (15 mL) is added potassium carbonate (1.29 g, 9.34 mmol) at room temperature. The reaction mixture is heated at 80° C. for 16 hours. The mixture is then quenched with water and extracted with EtOAc (2×70 mL). The organic extracts are washed with brine, dried over sodium sulphate, and evaporated under reduced pressure. The crude compound is purified by silica gel column chromatography (combiflash) eluting with 45% EtOAc in n-hexane to give the title compound (0.8 g, 54.27%). LCMS m/z 474.41 (M+H)$^+$.

Preparation 82

((S)-3-(4-{8-[4-(3-Hydroxy-3-methyl-butoxy)-2,6-dimethyl-phenyl]-2-isopropyl-[1,2,4]triazolo[1,5-a]pyridin-6-ylmethoxy}-phenyl)-hex-4-ynoic acid ethyl ester

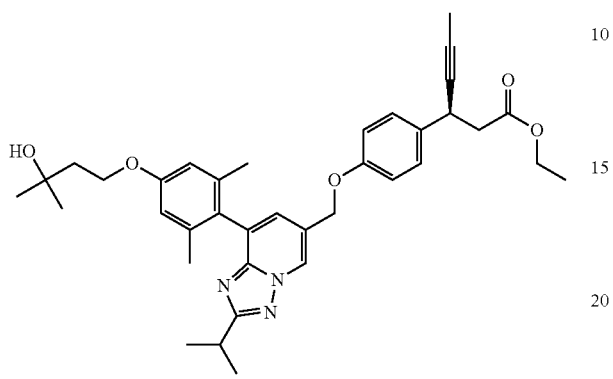

To a stirred solution of ((S)-3-(4-{8-[4-(3-hydroxy-3-methyl-butoxy)-2,6-dimethyl-phenyl]-2-isopropyl-[1,2,4]triazolo[1,5-a]pyridin-6-ylmethoxy}-phenyl)-hex-4-ynoicacidethylester (0.09 g, 0.17 mmol) in acetonitrile (10 mL) is added 4-bromo-2-methyl-butan-2-ol (0.114 g, 0.68 mmol) and cesium carbonate (0.168 g, 0.51 mmol). The reaction mixture is stirred at 100° C. for 4 hours. The reaction mixture is dissolved in water (10 mL) and extracted with EtOAc (2×20 mL). The combined organic extracts are washed with water (10 mL) and brine (10 mL), dried over anhydrous sodium sulphate, filtered, and evaporated. The crude material is purified by silica gel column chromatography eluting with 40% EtOAc in hexanes to give the title compound as brown solid (0.05 g, 50%). LC-MS m/z 612 [M+H]$^+$.

Preparation 83

(S)-3-(4-{8-[4-(3-Cyano-3,3-dimethyl-propoxy)-2,6-dimethyl-phenyl]-2-isopropyl-[1,2,4]triazolo[1,5-a]pyridin-6-ylmethoxy}-phenyl)-hex-4-ynoic acid ethyl ester

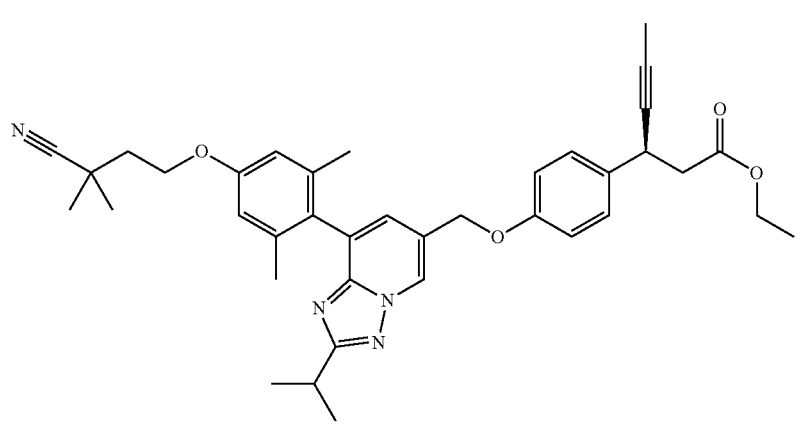 [SMILES: CC#C[C@@H](CC(=O)OCC)c1ccc(OCc2cc(-c3c(C)cc(OCCC(C)(C)C#N)cc3C)c3nc(C(C)C)nn3c2)cc1]

To a stirred solution of (S)-3-{4-[8-(4-hydroxy-2,6-dimethyl-phenyl)-2-isopropyl-[1,2,4]triazolo[1,5-a]pyridin-6-ylmethoxy]-phenyl}-hex-4-ynoic acid ethyl ester (0.16 g, 0.304 mmol) and 4-chloro-2,2-dimethylbutanenitrile (0.047 g, 0.364 mmol) in DMF (10 mL) is added cesium carbonate (0.29 g, 0.912 mmol) and stirred for 4 hours at 90° C. The reaction mixture is filtered through diatomaceous earth, the filtrate is diluted with water (30 mL), and extracted with EtOAc (2×30 mL). The combined organic extracts are washed with brine solution (2×30 mL), dried over anhydrous Na$_2$SO$_4$, and evaporated to dryness. The crude compound is purified by silica gel column chromatography (combiflash), eluting with 30% EtOAc/hexanes to give the title compound (0.17 g, 94%). ES/MS m/z 621.4 [M+H]$^+$.

Preparation 84

(S)-3-{4-[8-(4-Cyanomethoxy-2,6-dimethyl-phenyl)-2-isopropyl-[1,2,4]triazolo[1,5-a]pyridin-6-ylmethoxy]-phenyl}-hex-4-ynoic acid ethyl ester

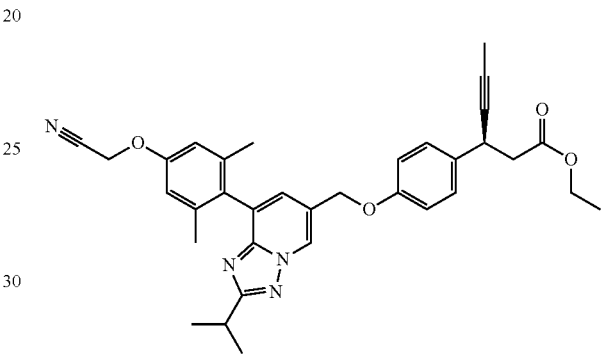

To a stirred solution of (S)-3-(4-{8-[4-hydroxy-2,6-dimethyl-phenyl]-2-isopropyl-[1,2,4]triazolo[1,5-a]pyridin-6-ylmethoxy}-phenyl)-hex-4-ynoic acid methyl ester (0.09 g, 0.17 mmol) in acetonitrile (10 mL) is added bromoacetonitrile (0.26 g, 0.22 mmol) and potassium carbonate (0.046 g, 0.34 mmol). The reaction mixture is stirred at 100° C. for 4 hours. The reaction mixture is diluted with water (10 mL) and extracted with EtOAc (2×20 mL). The combined organic extracts are washed with water (10 mL), brine (10 mL), dried over anhydrous sodium sulphate, filtered, and evaporated to dryness. The crude material is purified by silica gel column chromatography (combiflash), eluting with 35% EtOAc in hexanes to give the title compound as a brown solid (0.08 g, 82.4%). LC-MS m/z 565 [M+H]$^+$.

Example 1

(S)-3-{4-[2-Isopropyl-8-(4-methoxy-2,6-dimethyl-phenyl)-[1,2,4]triazolo[1,5-a]pyridin-6-ylmethoxy]-phenyl}-hex-4-ynoic acid

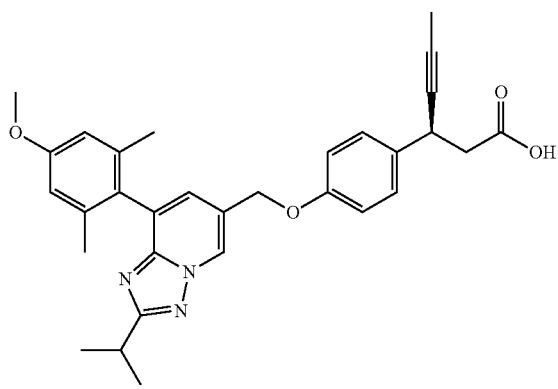 [SMILES: CC#C[C@@H](CC(=O)O)c1ccc(OCc2cc(-c3c(C)cc(OC)cc3C)c3nc(C(C)C)nn3c2)cc1]

To a solution of (S)-3-{4-[2-isopropyl-8-(4-methoxy-2,6-dimethyl-phenyl)-[1,2,4]triazolo[1,5-a]pyridin-6-yl-methoxy]-phenyl}-hex-4-ynoic acid ethyl ester (0.11 g, 0.2 mmol) in EtOH (15 mL) is added 5 N NaOH (0.12 mL, 0.61 mmol). The mixture is stirred at room temperature for 2 hours. The mixture is evaporated to dryness, the residue washed with n-pentane, dried and re-dissolved in water (5 mL). The solution is acidified with saturated citric acid solution to about pH 5. The solid precipitate is filtered, washed with water, and dried to give the title compound as a white solid (0.068 g, 65%). LCMS m/z 512 (M+H)$^+$. $^1$H NMR (400 MHz, d$_6$-DMSO) δ 12.17 (bs, 1H), 8.95 (s, 1H), 7.40 (s, 1H), 7.26 (t, J=8.0 Hz, 2H), 6.98 (d, J=8.4 Hz, 2H), 6.73 (s, 2H), 5.20 (s, 2H), 3.92 (s, 1H), 3.76 (s, 3H), 3.08 (t J=8.0 Hz, 2H), 2.65 (s, 2H), 1.89 (s, 6H), 1.75 (s, 3H), 1.27 (d, J=6.4 Hz, 6H).

The following compounds are prepared essentially by the method of Example 1.

TABLE 15

| Prep. No. | Chemical Name | Structure | ES/MS (m/z) (M + 1) |
|---|---|---|---|
| 2 | (S)-3-(4-{8-[4-(3-Hydroxy-3-methyl-butoxy)-2,6-dimethyl-phenyl]-2-isopropyl-[1,2,4]triazolo[1,5-a]pyridin-6-ylmethoxy}-phenyl)-hex-4-ynoic acid | 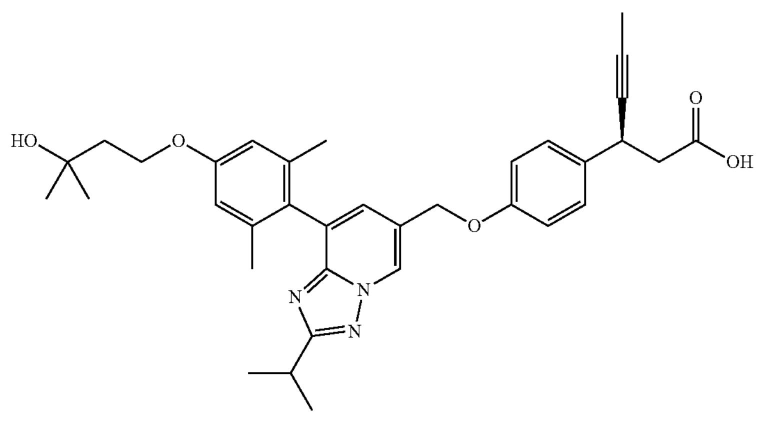 [SMILES: CC#C[C@@H](CC(=O)O)c1ccc(OCc2cc(-c3c(C)cc(OCCC(C)(C)O)cc3C)c3nc(C(C)C)nn3c2)cc1] | 584 |
| 3 | (S)-3-{4-[8-(2-Fluoro-5-methoxy-phenyl)-2-isopropyl-[1,2,4]triazolo[1,5-a]pyridin-6-ylmethoxy]-phenyl}-hex-4-ynoic acid | 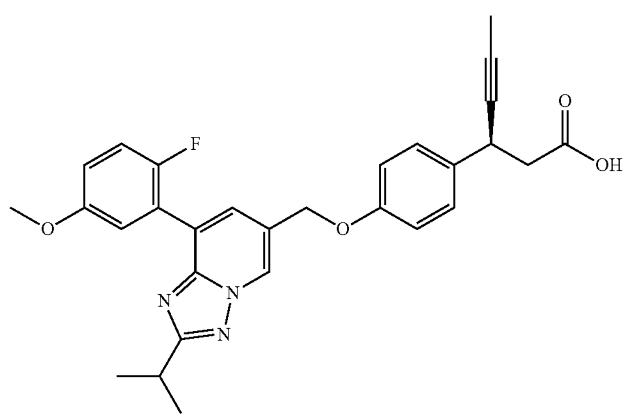 [SMILES: CC#C[C@@H](CC(=O)O)c1ccc(OCc2cc(-c3cc(OC)ccc3F)c3nc(C(C)C)nn3c2)cc1] | 502 |

TABLE 15-continued

| Prep. No. | Chemical Name | Structure | ES/MS (m/z) (M + 1) |
|---|---|---|---|
| 4 | (S)-3-(4-{2-Isopropyl-8-[4-(2-methoxy-ethoxy)-2,6-dimethyl-phenyl]-[1,2,4]triazolo[1,5-a]pyridin-6-ylmethoxy}-phenyl)-hex-4-ynoic acid | 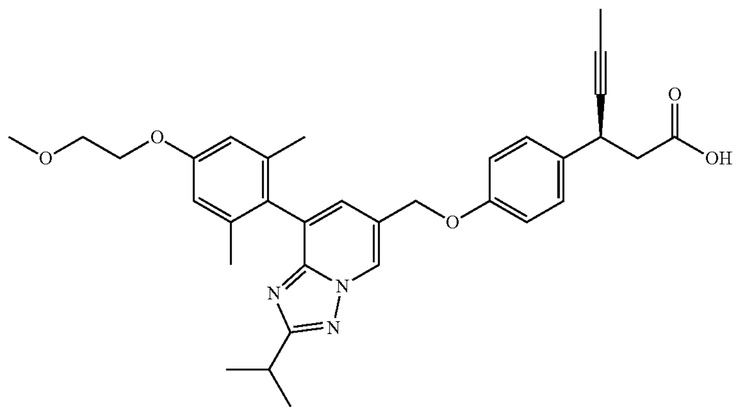 [SMILES: CC#C[C@@H](CC(=O)O)c1ccc(OCc2cc(-c3c(C)cc(OCCOC)cc3C)c3nc(C(C)C)nn3c2)cc1] | 556 |
| 5 | (S)-3-{4-[8-(2,6-Dimethyl-phenyl)-2-isopropyl-[1,2,4]triazolo[1,5-a]pyridin-6-ylmethoxy]-phenyl}-hex-4-ynoic acid | 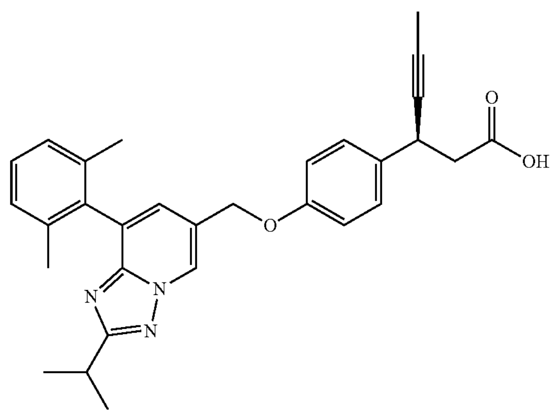 [SMILES: CC#C[C@@H](CC(=O)O)c1ccc(OCc2cc(-c3c(C)cccc3C)c3nc(C(C)C)nn3c2)cc1] | 482 |

Alternate Preparation, Example 1

To a solution of (S)-3-{4-[2-isopropyl-8-(4-methoxy-2,6-dimethyl-phenyl)-[1,2,4]triazolo[1,5-a]pyridin-6-yl-methoxy]-phenyl}-hex-4-ynoic acid ethyl ester (419 g, 0.776 mol) in EtOH (8.38 L) and THF (1 L) is added a solution of NaOH (62.1 g, 1.55 mol) in water (310 mL) at 10-15° C. The reaction mixture is warmed to 25° C. and stirred for 2 hours. Additional solution of NaOH (31.05 g, 0.78 mol) in water (155 mL) is added and the reaction is stirred for another 1.5 hours. The reaction mixture is evaporated to dryness to give a viscous material which is diluted with water (4.5 L) and washed with diethyl ether (3×2.5 L). The aqueous layer is cooled to 0° C. and acidified with saturated citric acid solution to pH 4.2 and stirred for 30 minutes. The resulting white emulsion is extracted with DCM (3×5 L). The combined organic extracts are washed with water (3×4 L) and brine (4 L), dried over anhydrous sodium sulphate, filtered, and evaporated to dryness to give a viscous oil. This oil is dissolved in DCM (5 L) and filtered to remove any particles that could be present. The resulting filtrate is concentrated to a viscous oil. Diethyl ether (2.5 L) is added followed by n-hexanes (5 L) and the mixture is stirred for 4 hours. From the resulting gummy material, the solvent is removed at 40° C. for 12 hours to give a light yellow solid as the title compound (341.9 g, 86%). LCMS m/z 512 (M+H)$^+$.

Tris Salt Preparation

The tris salt of (S)-3-{4-[8-(2,6-Dimethyl-phenyl)-2-isopropyl-[1,2,4]triazolo[1,5-a]pyridin-6-ylmethoxy]-phenyl}-hex-4-ynoic acid is prepared by dissolving (S)-3-{4-[8-(2,6-Dimethyl-phenyl)-2-isopropyl-[1,2,4]triazolo[1,5-a]pyridin-6-ylmethoxy]-phenyl}-hex-4-ynoic acid (492 mg) in acetonitrile (10 mL) while stirring at 80° C. (plate temp) at 1000 rpm. Tromethamine (tris) (492 mg) is added (dissolved in 1 mL of water). The sample is slurried at 80° C./1000 rpm for 15 minutes. Heat and stirring are turned off and the plate is permitted to reach room temperature. The stirring is resumed for a short time at room temperature. The sample is placed in the 5° C. refrigerator for 30 minutes after reaching room temperature. The white solid tris salt form is isolated by vacuum filtration and dried in place on the filter paper under vacuum and air stream for 15 minutes. The resulting sparkling white solid (due to the plate like morphology) is dried using the 70° C. vacuum oven. The resulting tris salt of (S)-3-{4-[8-(2,6-Dimethyl-phenyl)-2-isopropyl-[1,2,4]triazolo[1,5-a]pyridin-6-ylmethoxy]-phenyl}-hex-4-ynoic acid is recovered (458 mg, 74% yield).

Example 6

(S)-3-(4-((8-(2,6-Dimethyl-4-(3-(methylsulfonyl)
propoxy)phenyl)-2-isopropyl-[2,4]triazolo[1,5-a]
pyridin-6-yl)methoxy)phenyl)hex-4-ynoic acid

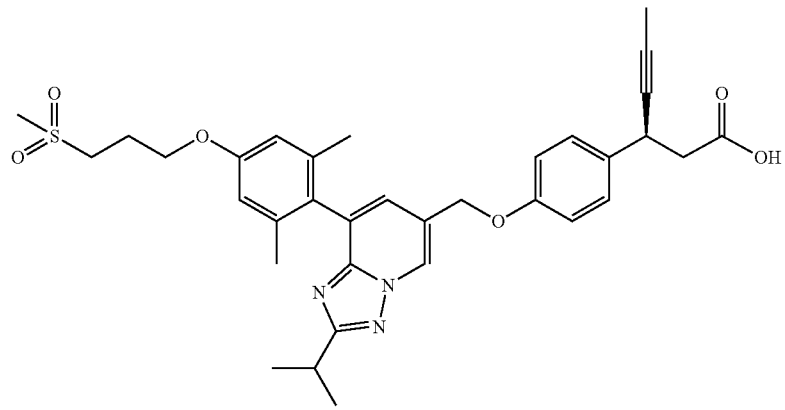 [SMILES: CC#C[C@@H](CC(=O)O)c1ccc(OCc2cc(-c3c(C)cc(OCCCS(C)(=O)=O)cc3C)c3nc(C(C)C)nn3c2)cc1]

To a stirred solution of (S)-ethyl 3-(4-((8-(2,6-dimethyl-4-(3-(methylsulfonyl)propoxy)phenyl)-2-isopropyl-[1,2,4]triazolo[1,5-a]pyridin-6-yl)methoxy)phenyl)hex-4-ynoate (0.200 g, 0.309 mmol) in EtOH (15 mL), is added 5 N sodium hydroxide (0.18 mL, 0.93 mmol). The reaction mixture is stirred at room temperature for 16 hours. The reaction mixture is concentrated and the residue is washed with diethyl ether (2×10 mL), dissolved in water (25 mL), and acidified with 1.0 N HCl (pH 4-5). The compound is extracted with DCM (2×25 mL) and the organic extracts are dried over anhydrous $Na_2SO_4$, filtered and concentrated to dryness. The crude material is further purified by prep HPLC. Prep HPLC conditions: Column: X BRIDGE C18 (19×250) mm, 5μ; Mobile phase (A): 0.1% TFA; Mobile phase (B): acetonitrile; Flow rate: gradient, 15 ml/min to give the title compound as a white solid (0.070 g, 36.64%). LCMS m/z 318.50 $(M+H)^+$.

Example 7

(S)-3-(4-{8-[4-(3-Cyano-3,3-dimethyl-propoxy)-2,6-
dimethyl-phenyl]-2-isopropyl-[1,2,4]triazolo[1,5-a]
pyridin-6-ylmethoxy}-phenyl)-hex-4-ynoic acid

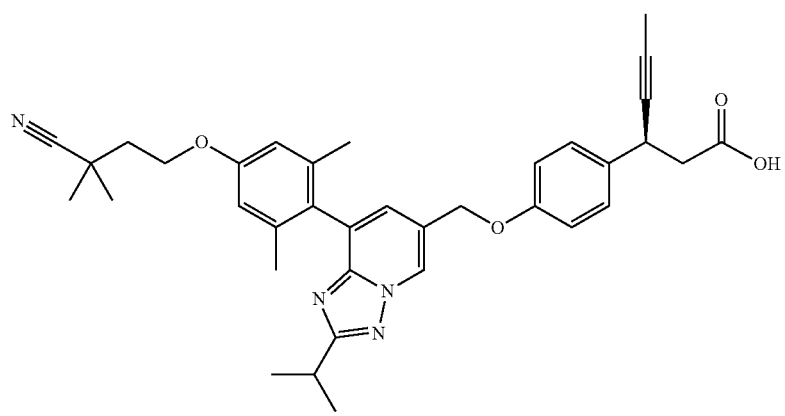 [SMILES: CC#C[C@@H](CC(=O)O)c1ccc(OCc2cc(-c3c(C)cc(OCCC(C)(C)C#N)cc3C)c3nc(C(C)C)nn3c2)cc1]

To a stirred solution of (S)-3-(4-{8-[4-(3-cyano-3,3-dimethyl-propoxy)-2,6-dimethyl-phenyl]-2-isopropyl-[1,2,4]triazolo[1,5-a]pyridin-6-ylmethoxy}-phenyl)-hex-4-ynoic acid ethyl ester (0.16 g, 0.258 mmol) in EtOH (10 mL) is added 5 N lithium hydroxide (0.15 mL, 0.774 mmol) and the mixture is stirred at 80° C. for 2 hours. The reaction mixture is concentrated under reduced pressure and the residue is triturated with ether/n-pentane (1:1). This material is dissolved in water and acidified with citric acid solution to about pH of 5. The solid precipitate is filtered and freeze dried to give the title compound as a white solid (0.145 g, 79.7%). LCMS m/z 593.4 [M+H]$^+$.

The following compounds are prepared essentially by the method of Example 7.

TABLE 16

| Prep. No. | Chemical Name | Structure | ES/MS (m/z) (M + 1) |
|---|---|---|---|
| 8 | (S)-3-(4-{8-[4-(Cyano-dimethyl-methyl)-phenyl]-2-isopropyl-[1,2,4]triazolo[1,5-a]pyridin-6-ylmethoxy}-phenyl)-hex-4-ynoic acid | 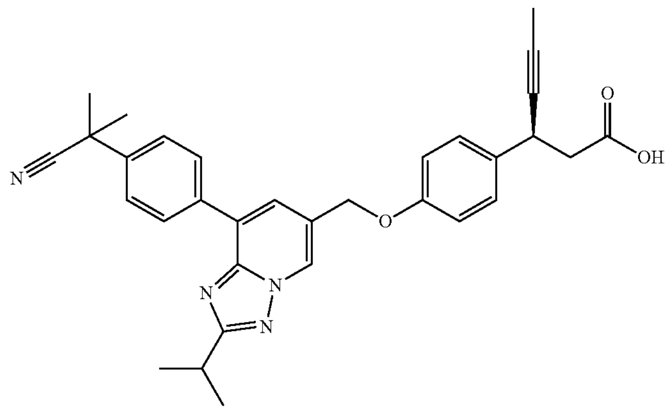 [SMILES: CC#C[C@@H](CC(=O)O)c1ccc(OCc2cc(-c3ccc(C(C)(C)C#N)cc3)c3nc(C(C)C)nn3c2)cc1] | 521 |

Example 9

(S)-3-(4-{8-[2-(Cyano-dimethyl-methyl)-phenyl]-2-isopropyl-[1,2,4]triazolo[1,5-a]pyridin-6-ylmethoxy}-phenyl)-hex-4-ynoic acid

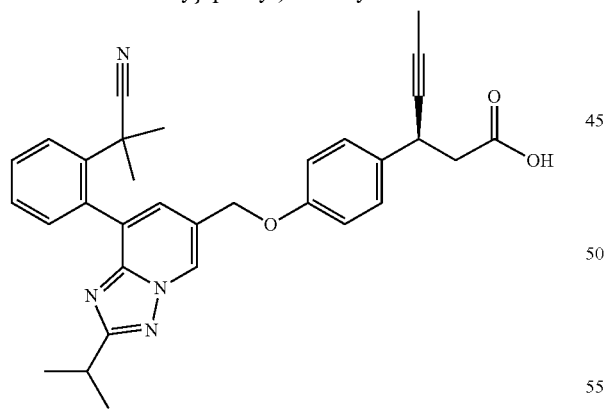

To a solution of (S)-3-(4-{8-[2-(cyano-dimethyl-methyl)-phenyl]-2-isopropyl-[1,2,4]triazolo[1,5-a]pyridin-6-ylmethoxy}-phenyl)-hex-4-ynoic acid ethyl ester (0.06 g, 0.109 mmol) in THF/water (6 mL/2 mL) is added 2 M LiOH (0.109 mL, 0.218 mmol). The mixture is stirred at room temperature for 12 hours. THF is evaporated under reduced pressure. The crude material is acidified with saturated citric acid solution (pH~5). The solid precipitate is then filtered and dried over vacuum to give the title compound as an off white solid (0.043 g, 75.7%). LC-MS m/z 521 [M+H]$^+$.

The following compounds are prepared essentially by the method of Example 9.

TABLE 17

| Prep. No. | Chemical Name | Structure | ES/MS (m/z) (M + 1) |
|---|---|---|---|
| 10 | (S)-3-{4-[8-(2-Cyano-phenyl)-2-isopropyl-[1,2,4]triazolo[1,5-a]pyridin-6-ylmethoxy]-phenyl}-hex-4-ynoic acid | 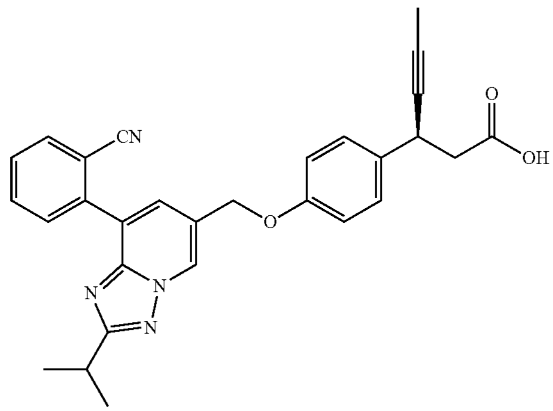 [SMILES: CC#C[C@@H](CC(=O)O)c1ccc(OCc2cc(-c3ccccc3C#N)c3nc(C(C)C)nn3c2)cc1] | 479 |
| 11 | (S)-3-{4-[8-(3-Cyano-phenyl)-2-isopropyl-[1,2,4]triazolo[1,5-a]pyridin-6-ylmethoxy]-phenyl}-hex-4-ynoic acid | 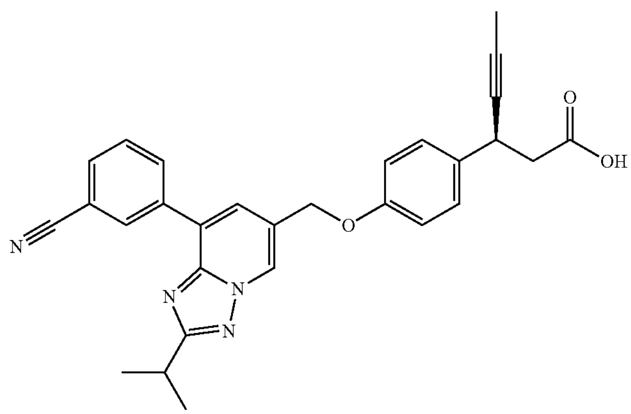 [SMILES: CC#C[C@@H](CC(=O)O)c1ccc(OCc2cc(-c3cccc(C#N)c3)c3nc(C(C)C)nn3c2)cc1] | 479 |

Example 12

((S)-3-{4-[8-(3-Cyanomethyl-phenyl)-2-isopropyl-[1,2,4]triazolo[1,5-a]pyridin-6-1methoxy]-phenyl}-hex-4-ynoic acid

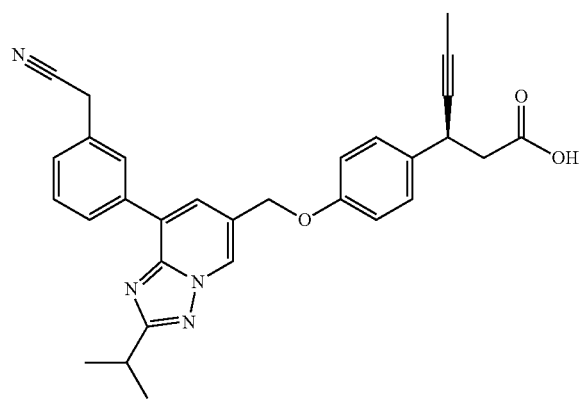 [SMILES: CC#C[C@@H](CC(=O)O)c1ccc(OCc2cc(-c3cccc(CC#N)c3)c3nc(C(C)C)nn3c2)cc1]

To a solution of (S)-3-(4-{8-[3-(cyano-dimethyl-methyl)-phenyl]-2-isopropyl-[1,2,4]triazolo[1,5-a]pyridin-6-yl-methoxy}-phenyl)-hex-4-ynoic acid ethyl ester (0.07 g, 0.13 mmol) in THF (7 mL) and water (3 mL) is added LiOH.H₂O (0.028 g, 0.67 mmol). The reaction mixture is stirred at room temperature for 48 hours. The reaction mixture is evaporated to dryness, then diluted with water (10 mL), acidified with citric acid (pH~5) and extracted with DCM (2×30 mL). The combined organic extracts are dried over anhydrous sodium sulphate and concentrated. The crude material is purified on silica gel column chromatography (combiflash), eluting with 15-50% EtOAc/hexanes to give the title compound (0.025 g, 29.41%). LCMS m/z 493.3 (M+H)⁺.

The following compounds are prepared essentially by the method of Example 12.

TABLE 18

| Prep. No. | Chemical Name | Structure | ES/MS (m/z) (M + 1) |
|---|---|---|---|
| 13 | (S)-3-[4-(3-Bromo-2-phenyl-pyrazolo[1,5-b]pyridazin-6-ylmethoxy)-phenyl]-3-isoxazol-3-yl-propionic acid | 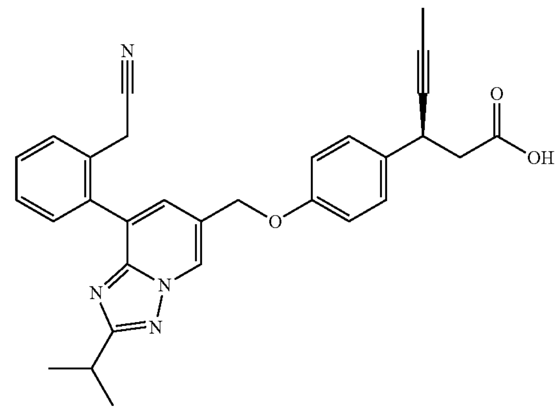 [SMILES: CC#C[C@@H](CC(=O)O)c1ccc(OCc2cc(-c3ccccc3CC#N)c3nc(C(C)C)nn3c2)cc1] | 493 |
| 14 | (S)-3-(4-{8-[3-(Cyano-dimethyl-methyl)-phenyl]-2-isopropyl-[1,2,4]triazolo[1,5-a]pyridin-6-ylmethoxy}-phenyl)-hex-4-ynoic acid | 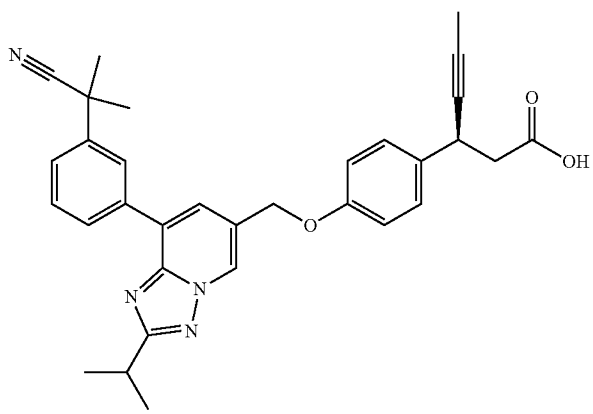 [SMILES: CC#C[C@@H](CC(=O)O)c1ccc(OCc2cc(-c3cccc(C(C)(C)C#N)c3)c3nc(C(C)C)nn3c2)cc1] | 521[a] |
| 15 | (S)-3-(4-{8-[3-(Cyano-dimethyl-methyl)-2-methyl-phenyl]-2-isopropyl-[1,2,4]triazolo[1,5-a]pyridin-6-ylmethoxy}-phenyl)-hex-4-ynoic acid | 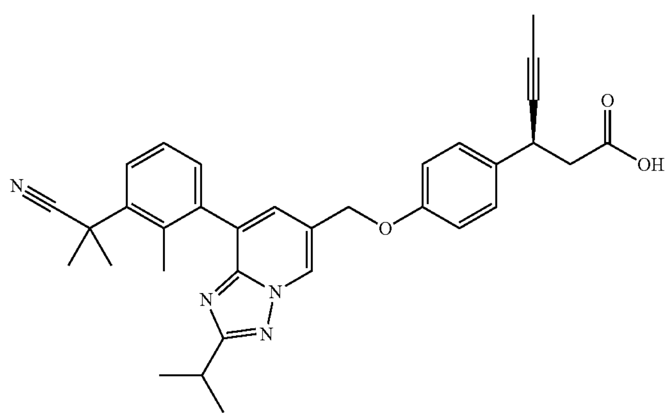 [SMILES: CC#C[C@@H](CC(=O)O)c1ccc(OCc2cc(-c3cccc(C(C)(C)C#N)c3C)c3nc(C(C)C)nn3c2)cc1] | 535 |

[a]Purified by preparative HPLC using column: Kinetex C18 (50 mm × 2.1 mm × 1.7 μm) with mobile phase (A) 0.01% TFA in water and (B) acetonitrile with flow rate of 0.3 mL/min

Example 16

(S)-3-{4-[8-(4-Cyanomethoxy-2,6-dimethyl-phenyl)-2-isopropyl-[1,2,4]triazolo[1,5-a]pyridin-6-ylmethoxy]-phenyl}-hex-4-ynoic acid

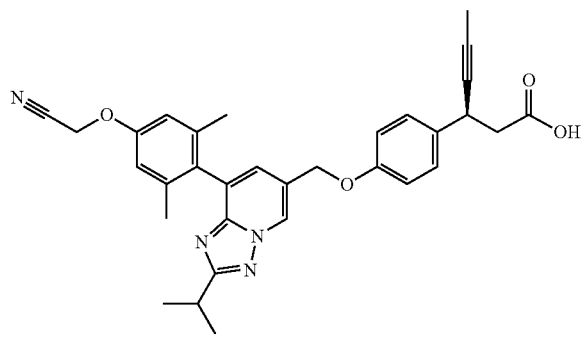 [SMILES: CC#C[C@@H](CC(=O)O)c1ccc(OCc2cc(-c3c(C)cc(OCC#N)cc3C)c3nc(C(C)C)nn3c2)cc1]

To a stirred solution of (S)-3-{4-[8-(4-cyanomethoxy-2,6-dimethyl-phenyl)-2-isopropyl-[1,2,4]triazolo[1,5-a]pyridin-6-ylmethoxy]-phenyl}-hex-4-ynoic acid ethyl ester (0.07 g, 0.12 mmol) in dichloroethane (10 mL) is added trimethyltin hydroxide (0.224 g, 1.23 mmol) and the mixture is heated at 80° C. for 96 hours. The reaction mixture is cooled to room temperature and washed with 1.5 N HCl solution (20 mL) and extracted with EtOAc (2×20 mL). The combined organic extracts are washed with saturated brine solution (10 mL), dried over sodium sulphate, filtered and concentrated. The crude material is purified on silica gel column chromatography (combiflash) eluting with 49% EtOAc/hexanes to give the title compound as a yellow solid (0.023 g, 34.8%). LCMS m/z 536 (M+H)$^+$.

The following compound is prepared essentially by the method of Example 16.

TABLE 19

| Prep. No. | Chemical Name | Structure | ES/MS (m/z) (M + 1) |
|---|---|---|---|
| 17 | (S)-3-{4-[8-(4-Cyanophenyl)-2-isopropyl-[1,2,4]triazolo[1,5-a]pyridin-6-ylmethoxy]-phenyl}-hex-4-ynoic acid | 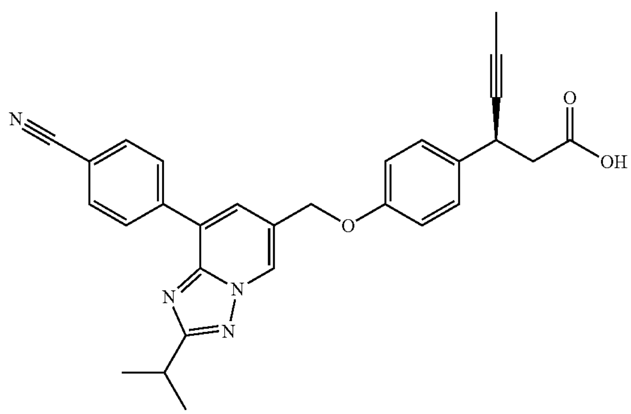 [SMILES: CC#C[C@@H](CC(=O)O)c1ccc(OCc2cc(-c3ccc(C#N)cc3)c3nc(C(C)C)nn3c2)cc1] | 479 |
| 18 | (S)-3-{4-[8-(4-Cyano-2,6-dimethyl-phenyl)-2-isopropyl-[1,2,4]triazolo[1,5-a]pyridin-6-ylmethoxy]-phenyl}-hex-4-ynoic acid | 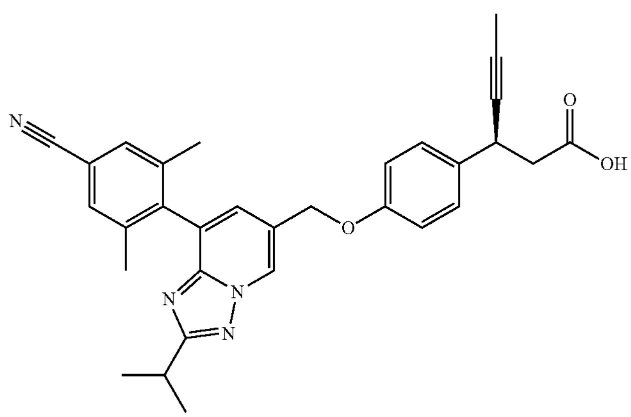 [SMILES: CC#C[C@@H](CC(=O)O)c1ccc(OCc2cc(-c3c(C)cc(C#N)cc3C)c3nc(C(C)C)nn3c2)cc1] | 507 |

GPR40: Information

Results of studies using transgenic mice over-expressing the human GPR40 gene under control of the insulin II promoter recently reported by Nagasumi further support that GPR40 plays an important role in the regulation of GDIS and plasma glucose levels in-vivo, especially in rodent models of insulin resistance. Nagasumi K, et. al., *Overexpression of GPR40 in pancreatic β-cells augments glucose-stimulated insulin secretion and improves glucose tolerance in normal and diabetic mice*, Diabetes 58: 1067-1076, 2009. See also, Briscoe C P et al., *The orphan G protein-coupled receptor GPR40 is activated by medium and long chain fatty acids*, Journal Biological Chemistry 278: 11303-11311, 2003. These findings further support that the development of new GPR40 modulator compounds may be particularly desired for use in the treatment of T2D.

Assays

Calcium Flux Primary Assays

The compounds exemplified herein are tested essentially as described below and exhibit an $EC_{50}$ value for the Calcium Flux Primary assay of lower than 500 nM, and exhibited efficacy of >50%.

These assays are used to screen compounds by measuring the increase in intracellular calcium levels that results when a ligand binds and activates GPR40, thus demonstrating the potency and efficacy of GPR40 agonists. HEK293 cells over expressing the human GPR40 cDNA maintained in Dulbecco's modified Eagle's medium with F12 medium in 3:1 ratio supplemented with 10% FBS and 800 µg/ml geneticin at 37° C. and 5% $CO_2$ are employed for the study. Agonist assays are performed using a Calcium 4 Dye assay kit (Molecular Devices) in the presence or absence of 0.1% fatty acid free BSA in the assay buffer (1×HBSS (Hank's Balanced Salt Solution) & 20 mM HEPES (4-(2-hydroxyethyl)-1-piperazineethanesulfonic acid). Receptor activation is measured as an increase in intracellular calcium using the Fluorometric Imaging Plate Reader (FLIPR). Maximum change in fluorescence over the base line is used to determine the agonist response. The $EC_{50}$ value of the compound is calculated using Excel Fit software (version 4; IDBS) by plotting concentration vs relative fluorescence units (RFUs). Percent efficacy is calculated based on the maximal response exhibited by compound compared to the natural ligand, linoleic acid. The test compound of Example 1 has an $EC_{50}$ of 247 nM (±23.9, n=12) and 78.7% efficacy (±12.5, n=12) when examined in this assay. These results further demonstrate the desired potency and efficacy of this compound as a GPR40 agonist. (Mean±SEM; SEM=standard error of the mean.)

Selectivity Assays

Peroxisome Proliferator-Activated Receptor (PPAR) α, δ, and γ Functional Assays Because GPR40 is known to be activated by ligands to PPARγ, exemplified compounds are examined in Gal4 PPARα, Gal4 PPARδ, and PPARγ reporter assays to determine the selectivity of exemplified compounds. CV1 cells, which are derived from the renal tissue of an African green monkey, are transfected with various receptor and reporter plasmids using Fugene. For the Gal4 PPARα and PPARδ assays, a reporter plasmid containing five tandem copies of the yeast transcription protein Gal4 response element, cloned upstream of a firefly luciferase gene driven by the major late promoter of adenovirus, is transfected together with a Simian Virus 40 (SV40) driven plasmid constitutively expressing a hybrid protein containing the Gal4 DNA binding domain (DBD), and either the PPARα or PPARδ ligand binding domain. For the PPARγ assay, plasmids encoding PPARγ and RXRα, both driven by a cytomegalovirus (CMV) promoter are transfected together with a plasmid containing luciferase reporter cDNA driven by the TK promoter and a receptor response element (2×PPRE). Cells are transfected in T225 $cm^2$ cell culture flasks in DMEM media with 5% charcoal-stripped FBS and the specific plasmids for the individual assay. After an overnight incubation, transfected cells are trypsinized, plated in opaque 96 well dishes (15,000 cells/well) in DMEM media containing 5% charcoal-stripped FBS, incubated for 4 hours, and exposed to 0.17 µM to 10 µM of test compounds or reference compound in half log dilutions. After 24 hours incubation with compounds, cells are lysed and luciferase activity is determined as a measure of receptor activation by luminescence. Data are fitted to a four parameter-fit logistics model to determine $EC_{50}$ values. The maximum percent stimulation is determined versus maximum stimulation obtained with 10 µM of an appropriated PPAR agonist reference compound, 2-methyl-2-(4-{2-methyl-3-[2-(phenylcarbonyl)-4-(trifluoromethoxy)phenoxy]propoxy}phenoxy)propanoic acid. Efficacy of <20% is considered negative. $EC_{50}$s for the compound of Example 1 in PPAR functional assays are as follows: PPARα>10 µM; PPARδ=4 µM; PPARγ=2.26 µM. These data indicate that the exemplified compound of Example 1 has weak PPAR activity. Thus, these assays support that the exemplified compounds have weak or negative PPAR efficacy in the assay described, as desired.

In Vitro Binding Affinity to GPR40

Radioligand competition binding assays using rapid-wash filtration with a custom prepared radiolabel (5 nM [$^3$H]-TAK-875) and membranes prepared from HEK293 cells overexpressing the human GPR40 (hGPR40) construct are run to determine equilibrium dissociation constants ($K_i$) for test compounds. Competition curves are plotted as the percent specific inhibition versus concentration of compound and analyzed using a four parameter nonlinear regression fit with variable slope. $K_i$ values are calculated using the Cheng-Prusoff equation $K_i=IC_{50}/(1+(D/K_d))$, where $IC_{50}$ is the concentration of compound resulting in 50% inhibition of binding, D is the concentration of radioligand used in the assay and $K_d$ is the equilibrium dissociation constant for the receptor and the radioligand, determined from saturation binding analysis experiments ($K_d$ for [$^3$H] TAK-875=6.2). For Example 1, $K_i$=15.8 nM±3.86, n=⅚. See Cheng, Y. and Prusoff, W. H. (1973) "Relationship between the inhibition constant ($K_i$) and the concentration of inhibitor which causes 50 percent inhibition ($IC_{50}$) of an enzymatic reaction", *Biochem Pharmacol* 22(23):3099-108. (Mean±SEM; SEM=standard error of the mean.) These data demonstrate that the Example 1 compound is a high affinity ligand for human GPR40.

Competition Binding Kinetics—Determination of Receptor Residence Time

The association and dissociation rates of unlabeled compounds are quantified using the method described by Motulsky, H. J. and L. C. Mahan (1984), "The kinetics of competitive radioligand binding predicted by the law of mass action" *Mol Pharm* 25(1): 1-9. Human GPR40 membranes are incubated at various time points with 6-8 nM [$^3$H] TAK875 in the absence or presence of 1× $K_i$, 3× $K_i$, or 10× $K_i$ unlabeled compound. Separation of bound and free radio-ligand is performed using rapid-wash filtration onto glass fiber filters and counted in a liquid scintillation counter. Rates are calculated by fitting the data to the kinetics of competitive binding model in GraphPad Prism 6, version 6.03 for Windows, GraphPad Software, La Jolla Calif. USA, www.graphpad.com. The compound of Example 1 showed a GPR40 Residence time, τ, to be 169 min (±52.1, n=4), which suggests that this GPR40 ligand has sufficient residence time on the receptor to produce an in-vivo response (Mean±SEM; SEM=standard error of the mean.)

Human and Mouse Beta-Arrestin Agonist Assay with 1% FBS to Determine Beta-Arrestin Recruitment Human embryonic kidney (hEK293)-hFFAR1 cells are purchased from DiscoveRx. Human osteosarcoma (U205) cells expressing mFFAR1 are developed by DiscoveRX. These cells co-express the Prolink (PK)-tagged GPR40 and the Enzyme Acceptor (EA)-tagged beta-arrestin fusion proteins. If activation of the GPR40 stimulates beta-arrestin recruitment, it would force complementation of the beta galactosidase (B-gal) enzyme fragments, forming a B-gal enzyme that generates a chemiluminescent signal using the DiscoveRx PathHunter detection kit. Cells are incubated overnight at 5,000 cells/well in 384 well plates in culture media containing 1% FBS (fetal bovine serum). Serial diluted compounds in DMSO (2× dilutions to generate 20 concentrations) are step down diluted in culture media containing 1% FBS (fetal bovine serum) and added to cells with a final top concentration starting of 100 μM. After addition of compounds, cells are incubated for 90 min at 37° C. in 5% $CO_2$ incubator, and DiscoveRX kit detection reagents are added. Measurement of the chemiluminescent signal is ascertained with the Envision reader, after a 1-hour incubation at room temperature. Data are fit to a 4 parameter-fit logistics to determine $EC_{50}$ values, % activity is measured versus maximum response to an internal standard GPR40 agonist standard, TAK875, at 1 μM. Example 1, has an hGPR40 b-arrestin $EC_{50}$ of 30.6 nM (±12.3, n=2) with a % stimulation max (FA) of 170 (±5.95, n=2) and mGPR40 b-arrestin of 4.87 nM (±1.48, n=3) with a % stimulation max (FA) of 149 (±11.8, n=3). (Mean+SEM; SEM=standard error of the mean.) These data indicate that Example 1 is a GPR40 agonist which can signal through beta arrestin.

The exemplified compounds of the present invention can be readily formulated into pharmaceutical compositions in accordance with accepted practices known in the art such as found in Remington's "Pharmaceutical Sciences", Gennaro, Ed., Mack Publishing Co. Easton Pa. 1990 such as tablets, solid or gel filled capsules, powders, suspensions, or solutions. The composition can also include one or more pharmaceutically acceptable carriers, excipients, and diluents.

Preferred pharmaceutical compositions include those formulated as a tablet or capsule for oral administration. The tablet or capsule can include a compound of the present invention in an amount effective to treat diabetes particularly type two diabetes. The artisan will appreciate that a compound of Formula I may be administered with one or more additional therapeutic agents. It may be preferred that pharmaceutical compositions are formulated to include a compound of Formula I and one or more additional therapeutic agents.

The pharmaceutical composition is administered to a patient in amounts effective to treat diabetes, more particularly, type two diabetes. An appropriate amount or dose effective to treat a patient can be determined by a health care provider.

What is claimed is:
1. A compound which is:

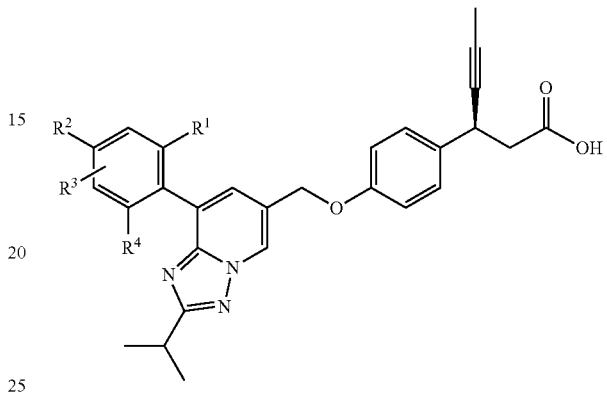

wherein
$R^1$ is selected from the group consisting of H, $CH_3$, CN, $CH_2CN$, $C(CH_3)_2CN$, and F;
$R^2$ is selected from the group consisting of H, —O($C_1$-$C_3$alkyl)$R^5$, $CH_2CN$, and CN;
$R^3$ is selected from the group consisting of H, $OCH_3$, CN, $C(CH_3)_2CN$, and $CH_2CN$;
$R^4$ is selected from the group consisting of H and $CH_3$; and
$R^5$ is selected from the group consisting of H, CN, $C(CH_3)_2CN$, $OCH_3$, $S(O)_2CH_3$, and $C(CH_3)_2OH$; provided that at least one selected from the group consisting of $R^1$, $R^2$, $R^3$, and $R^4$ is H;
or a pharmaceutically acceptable salt thereof.

2. A compound or pharmaceutically acceptable salt thereof as claimed by claim 1 wherein $R^3$ is H.

3. A compound or pharmaceutically acceptable salt thereof as claimed by claim 2 wherein $R^1$ is selected from the group consisting of H and $CH_3$.

4. A compound or pharmaceutically acceptable salt thereof as claimed by claim 3 wherein $R^2$ is selected from the group consisting of H and $_2O(C_1$-$C_3$alkyl)$R^5$.

5. A compound or pharmaceutically acceptable salt thereof as claimed by claim 4 wherein $R^2$ is selected from the group consisting of H and $OCH_3$.

6. A compound or pharmaceutically acceptable salt thereof as claimed by claim 5 wherein $R^4$ is $CH_3$.

7. A compound or pharmaceutically acceptable salt thereof as claimed by claim 6 wherein $R^1$ is $CH_3$.

8. A compound as claimed by claim 1 that is (S)-3-{4-[2-Isopropyl-8-(4-methoxy-2,6-dimethyl-phenyl)-[1,2,4]triazolo[1,5-a]pyridin-6-ylmethoxy]-phenyl}-hex-4-ynoic acid, or a pharmaceutically acceptable salt thereof.

9. A compound as claimed by claim 1 that is (S)-3-[4-{8-(2,6-Dimethyl-phenyl)-2-isopropyl-[1,2,4]triazolo[1,5-a]pyridin-6-ylmethoxy]-phenyl}-hex-4-ynoic acid or a pharmaceutically acceptable salt thereof.

10. A pharmaceutical composition comprising a compound according to claim 1, or a pharmaceutically acceptable salt thereof, and at least one of a pharmaceutically acceptable carrier, diluent, or excipient.

11. A method of treating diabetes in a mammal in need thereof, comprising administering an effective amount of a compound, or a pharmaceutically acceptable salt thereof, as claimed by claim 1.

12. A method of treating type two diabetes in a mammal in need thereof, comprising administering an effective amount of a compound, or a pharmaceutically acceptable salt thereof as claimed by claim 1.

13. A compound according to formula II

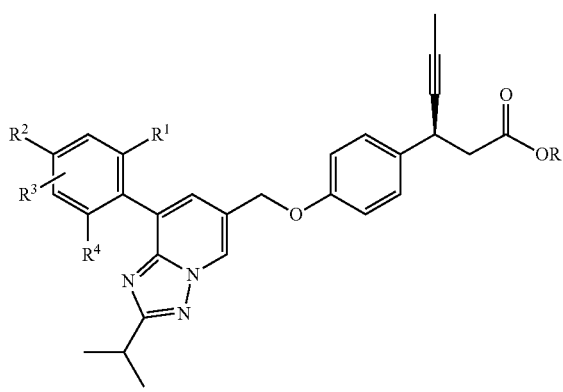

wherein $R^1$ is selected from the group consisting of H, $CH_3$, CN, $CH_2CN$, $C(CH_3)_2CN$, and F;

$R^2$ is selected from the group consisting of H, —O($C_1$-$C_3$alkyl)$R^5$, $CH_2CN$, and CN;

$R^3$ is selected from the group consisting of H, $OCH_3$, CN, $C(CH_3)_2CN$, and $CH_2CN$;

$R^4$ is selected from the group consisting of H and $CH_3$;

$R^5$ is selected from the group consisting of H, CN, $C(CH_3)_2CN$, $OCH_3$, $S(O)_2CH_3$, and $C(CH_3)_2OH$; provided that at least one selected from the group consisting of $R^1$, $R^2$, $R^3$, and $R^4$ is H; and R is selected from the group consisting of $C_{1-4}$ alkyl, $C_{1-4}$ haloalkyl, $C_{3-6}$ cycloalkyl, $C_{1-4}$ alkyl-$C_{3-6}$ cycloalkyl, phenyl, and $C_{1-5}$ alkylphenyl, or a pharmaceutically acceptable salt thereof.

14. A compound of claim 13 wherein $R^1$ and $R^4$ are each $CH_3$.

15. A compound of claim 13 wherein $R^1$ and $R^4$ are each H.

16. A compound as claimed claim 13 wherein $R^2$ is selected from the group consisting of H and $OCH_3$.

17. A method for preparing a compound of Formula I, below,

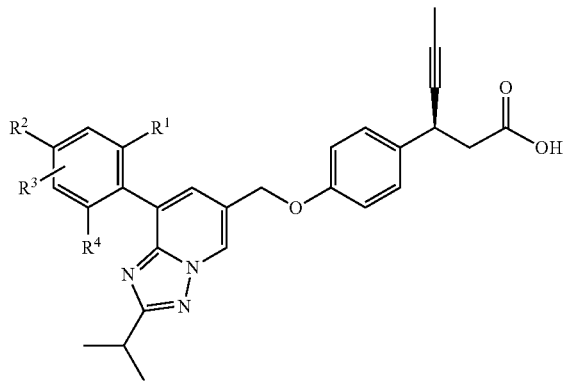

or a pharmaceutically acceptable salt thereof, said method comprising de-esterifying a compound of formula II;

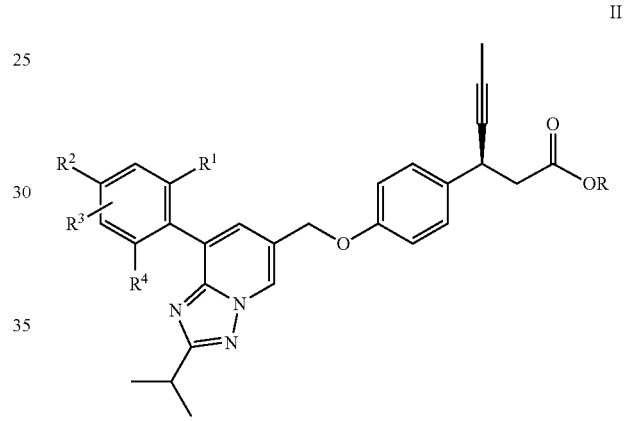

wherein $R^1$ is selected from the group consisting of H, $CH_3$, CN, $CH_2CN$, $C(CH_3)_2CN$, and F;

$R^2$ is selected from the group consisting of H, —O($C_1$-$C_3$alkyl)$R^5$, $CH_2CN$, and CN;

$R^3$ is selected from the group consisting of H, $OCH_3$, CN, $C(CH_3)_2CN$, and $CH_2CN$;

$R^4$ is selected from the group consisting of H and $CH_3$;

$R^5$ is selected from the group consisting of H, CN, $C(CH_3)_2CN$, $OCH_3$, $S(O)_2CH_3$, and $C(CH_3)_2OH$; provided that at least one selected from the group consisting of $R^1$, $R^2$, $R^3$, and $R^4$ is H; and R is selected from the group consisting of $C_{1-4}$ alkyl, $C_{1-4}$ haloalkyl, $C_{3-6}$ cycloalkyl, $C_{1-4}$ alkyl-$C_{3-6}$ cycloalkyl, phenyl, and $C_{1-5}$ alkylphenyl to provide a compound of Formula I, or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 9,809,592 B2 | Page 1 of 1 |
| APPLICATION NO. | : 15/106953 | |
| DATED | : November 7, 2017 | |
| INVENTOR(S) | : Chafiq Hamdouchi, Pranab Maiti and Anne Reifel Miller | |

It is certified that error appears in the above-identified patent and that said Letters Patent is hereby corrected as shown below:

In Column 74, Line 48, in Claim 4, delete "$_2O(C_1-C_3alkyl)R^5$." and insert -- -$O(C_1-C_3alkyl)R^5$.--, therefor.

In Column 74, Lines 60-61, in Claim 9, delete "(S)-3-[4-{8-(2,6-" and insert --(S)-3-{4-[8-(2,6- --, therefor.

In Column 75, Line 54, in Claim 16, after "claimed" insert --by--.

Signed and Sealed this
Twenty-second Day of May, 2018

Andrei Iancu
*Director of the United States Patent and Trademark Office*